US010828638B2

(12) United States Patent
Kerns et al.

(10) Patent No.: US 10,828,638 B2
(45) Date of Patent: Nov. 10, 2020

(54) IN VITRO EPITHELIAL MODELS COMPRISING LAMINA PROPRIA-DERIVED CELLS

(71) Applicant: EMULATE, Inc., Boston, MA (US)

(72) Inventors: S. Jordan Kerns, Reading, MA (US); Riccardo Barrile, Boston, MA (US); Geraldine Hamilton, Boston, MA (US); Catherine Karalis, Brookline, MA (US); Daniel Levner, Brookline, MA (US); Carolina Lucchesi, Westwood, MA (US); Antonio Varone, West Roxbury, MA (US); Remi Villenave, Boston, MA (US)

(73) Assignee: Emulate, Inc., Boston, MA (US)

( * ) Notice: Subject to any disclaimer, the term of this patent is extended or adjusted under 35 U.S.C. 154(b) by 245 days.

(21) Appl. No.: 15/819,435

(22) Filed: Nov. 21, 2017

(65) Prior Publication Data

US 2018/0185844 A1 Jul. 5, 2018

Related U.S. Application Data

(60) Provisional application No. 62/429,487, filed on Dec. 2, 2016.

(51) Int. Cl.
*B01L 3/00* (2006.01)
*G01N 33/48* (2006.01)
(Continued)

(52) U.S. Cl.
CPC ... *B01L 3/502753* (2013.01); *B01L 3/502715* (2013.01); *C12M 23/16* (2013.01);
(Continued)

(58) Field of Classification Search
CPC ... C12N 5/0636; C12M 23/16; C12M 5/0636; B01L 3/502753; B01L 3/502715; B01L 3/00; G01N 33/48; G01N 35/00
See application file for complete search history.

(56) References Cited

U.S. PATENT DOCUMENTS

| 8,647,861 B2 | 2/2014 | Ingber et al. ............... 435/289.1 |
| 8,940,701 B2 | 1/2015 | Livant ........................... 514/19.3 |

(Continued)

FOREIGN PATENT DOCUMENTS

| WO | WO/2010/009307 | 1/2010 |
| WO | WO/2012/118799 | 9/2012 |

(Continued)

OTHER PUBLICATIONS

Bischel, L. L. et al. (2012) "A Practical Method for Patterning Lumens through ECM Hydrogels via Viscous Finger Patterning," *Journal of Laboratory Automation* 17(2), 96-103.

(Continued)

*Primary Examiner* — Brian J. Sines
(74) *Attorney, Agent, or Firm* — Medlen & Carroll, LLP

(57) ABSTRACT

An in vitro microfluidic "organ-on-chip" is described herein that mimics the structure and at least one function of specific areas of the epithelial system in vivo. In particular, a multicellular, layered, microfluidic culture is described, allowing for interactions between lamina propria-derived cells and the associated tissue specific epithelial cells and endothelial cells. This in vitro microfluidic system can be used for modeling inflammatory tissue, e.g., autoimmune disorders involving epithelia and diseases involving epithelial layers. These multicellular, layered microfluidic "organ-on-chip", e.g. "epithelia-on-chip" further allow for comparisons between types of epithelia tissues, e.g., lung (Lung-On-Chip), bronchial (Airway-On-Chip), skin (Skin-On-Chip), cervix (Cervix-On-Chip), blood brain barrier (BBB- (Continued)

On-Chip), etc., in additional to neurovascular tissue, (Brain-On-Chip), and between different disease states of tissue, i.e. healthy, pre-disease and diseased areas. Additionally, these microfluidic "organ-on-chips" allow identification of cells and cellular derived factors driving disease states in addition to drug testing for reducing inflammation effecting epithelial regions.

26 Claims, 25 Drawing Sheets

(51) Int. Cl.
    *G01N 35/00*     (2006.01)
    *C12M 1/00*     (2006.01)
    *C12M 3/06*     (2006.01)
    *C12M 1/42*     (2006.01)
    *G01N 33/50*     (2006.01)
    *C12N 5/00*     (2006.01)

(52) U.S. Cl.
    CPC ............ *C12M 29/04* (2013.01); *C12M 35/08* (2013.01); *G01N 33/5044* (2013.01); *C12N 5/0018* (2013.01); *C12N 5/0075* (2013.01)

(56) References Cited

U.S. PATENT DOCUMENTS

| | | | | |
|---|---|---|---|---|
| 2013/0164279 A1* | 6/2013 | Goel | ............ | C12Q 1/6886 424/133.1 |
| 2014/0212910 A1* | 7/2014 | Bhatia | ............ | C12N 5/0062 435/29 |
| 2014/0302491 A1 | 10/2014 | Nadauld et al. | ............ | 435/5 |
| 2016/0243738 A1 | 8/2016 | Katrycz | ............ | 264/294 |
| 2016/0326477 A1 | 11/2016 | Fernandez-Alcon et al. | ............ | 435/29 |
| 2017/0285003 A1* | 10/2017 | Hamilton | ............ | C12M 23/16 |
| 2018/0185844 A1* | 7/2018 | Kerns | ............ | G01N 33/5044 |
| 2018/0224432 A1* | 8/2018 | Kerns | ............ | C12N 5/0697 |

FOREIGN PATENT DOCUMENTS

| | | |
|---|---|---|
| WO | WO/2013/086486 | 6/2013 |
| WO | WO/2013/086502 | 6/2013 |
| WO | WO/2015/013332 | 1/2015 |
| WO | WO/2015/138032 | 9/2015 |
| WO | WO/2015/138034 | 9/2015 |

OTHER PUBLICATIONS

Wu, W. et al. (2011) "Omnidirectional Printing of 3D Microvascular Networks," *Advanced Materials* 23(24), H178-H183.

Wu, W. et al. (2010) "Direct-write assembly of biomimetic microvascular networks for efficient fluid transport," *Soft Matter* 6(4), 739-742.

PCT International Search Report of International Application No. PCT/US2017/062817 dated Apr. 24, 2018.

* cited by examiner

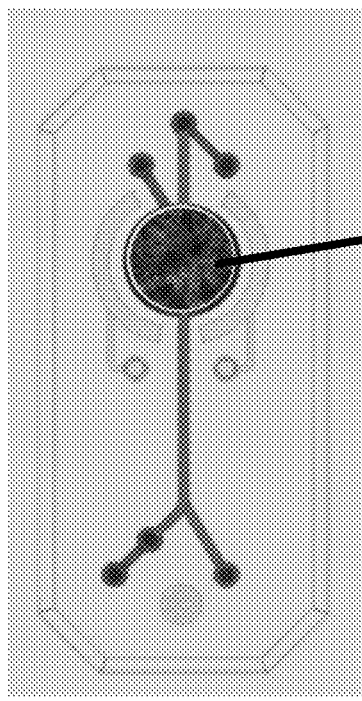
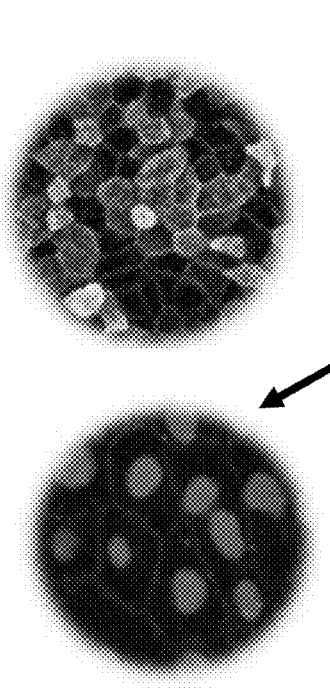
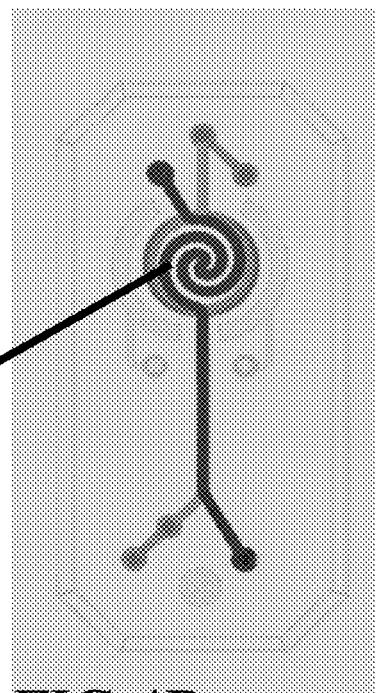
FIG.4A
FIG.4B
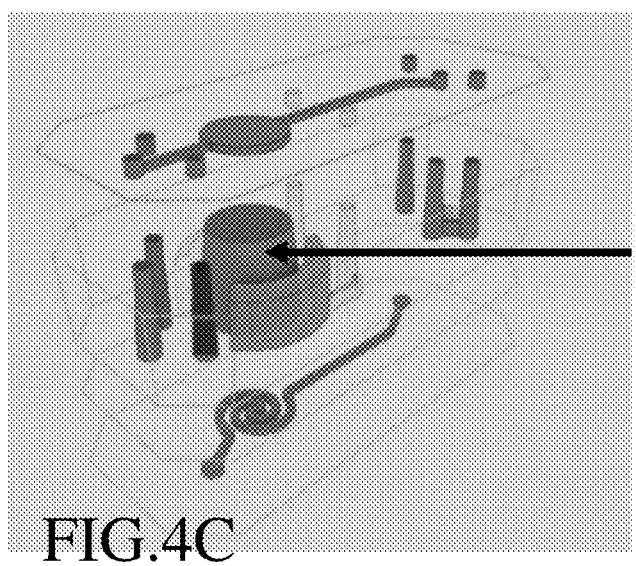
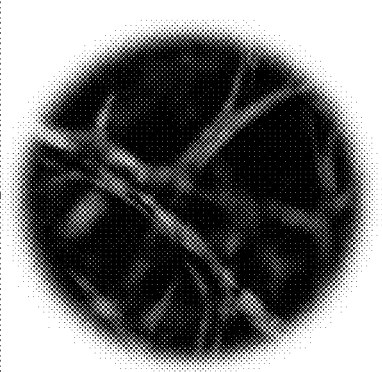
FIG.4C

FIGURE 8A – 8B
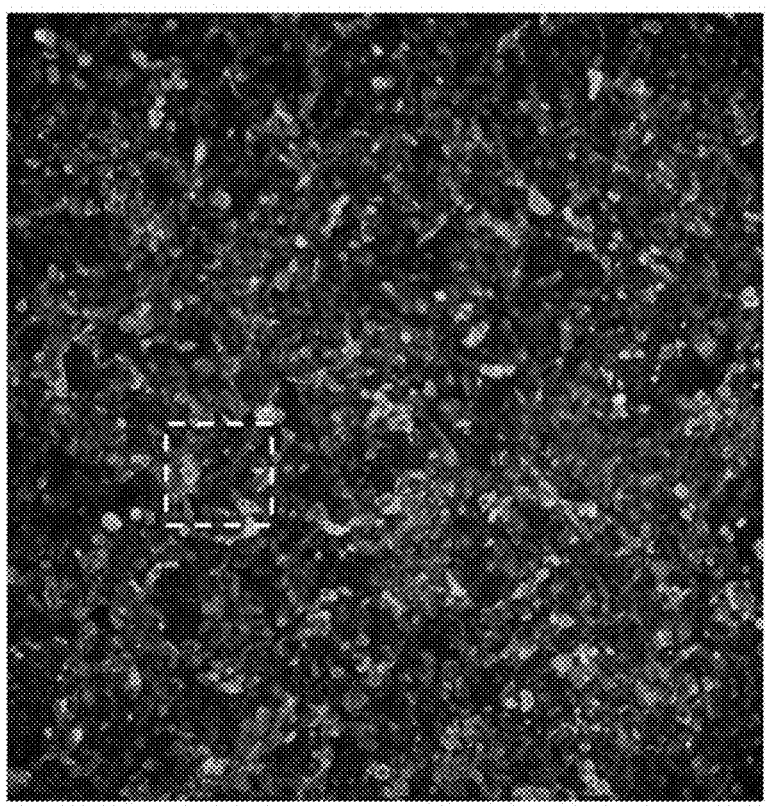
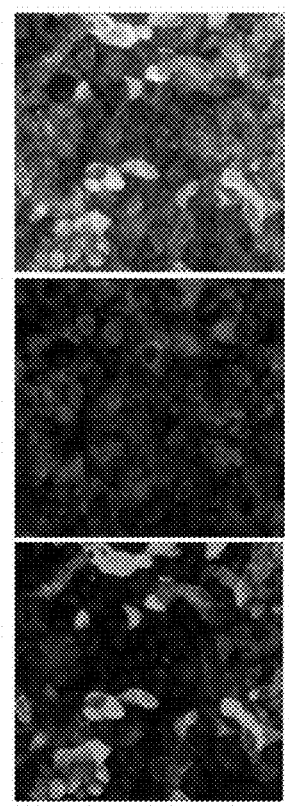
FIG.8A　　　　　　　　　　FIG.8B

FIGURE 9A – 9B
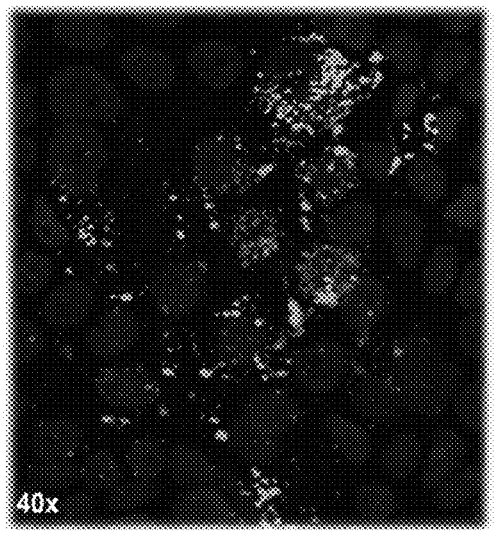
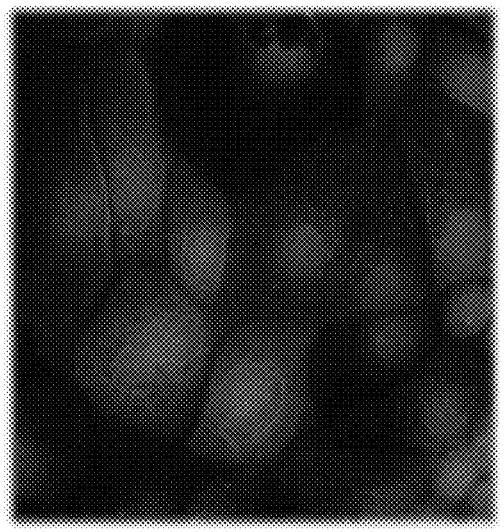
FIG.9A  FIG.9B

FIGURE 10A – 10C
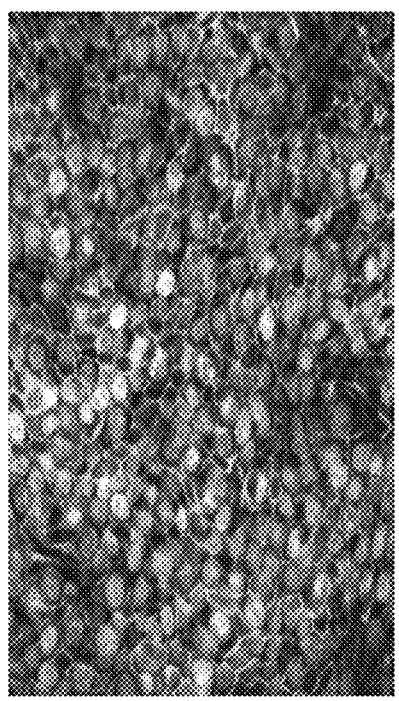
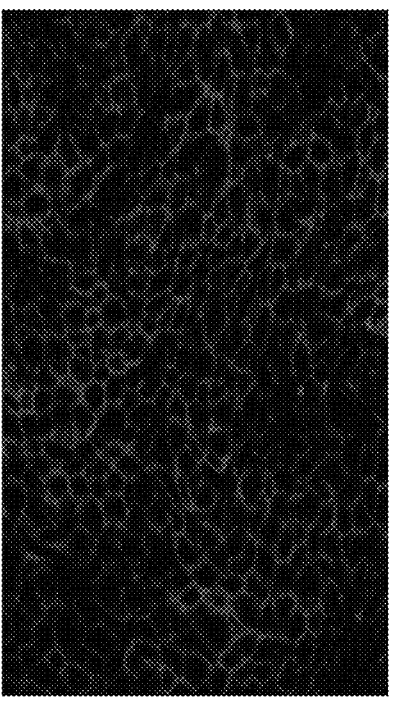
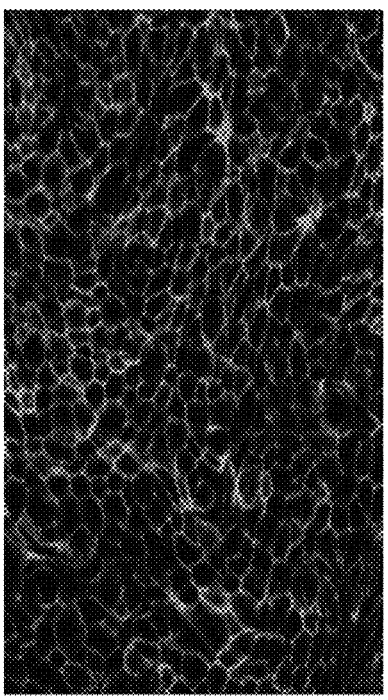
FIG.10A    Fig.10B    Fig.10C

FIGURE 12A – 12B
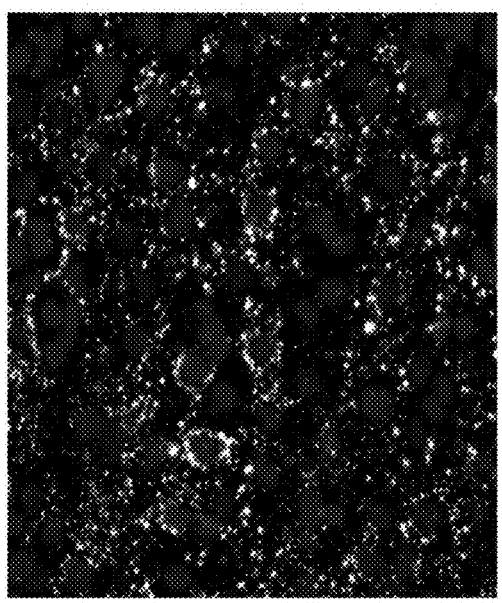
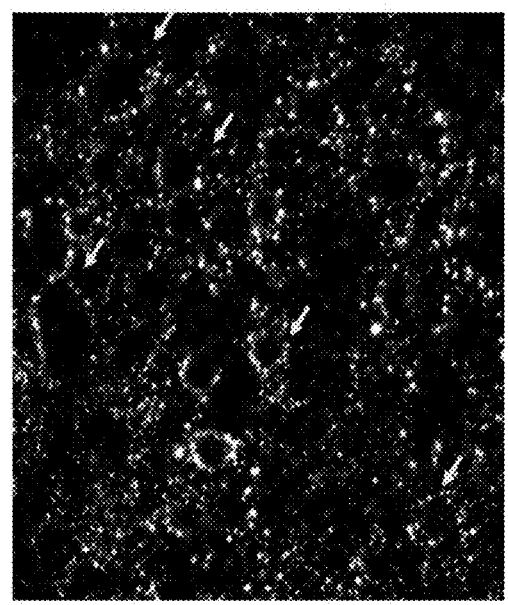
FIG.12A  FIG.12B

FIGURE 14A – 14C
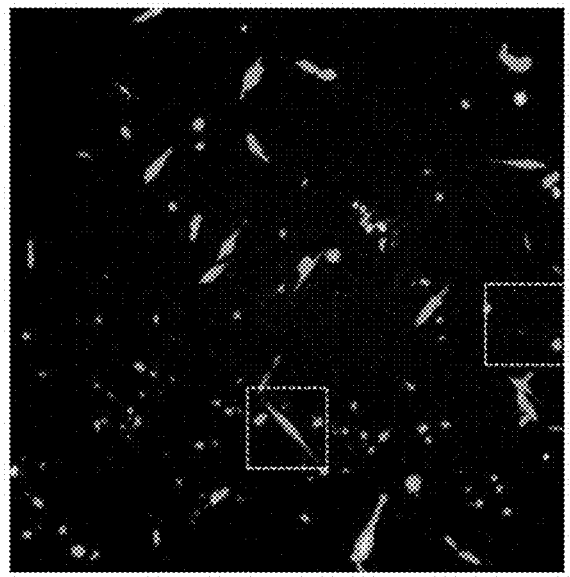
FIG.14A
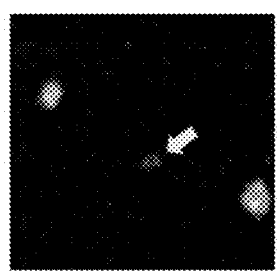
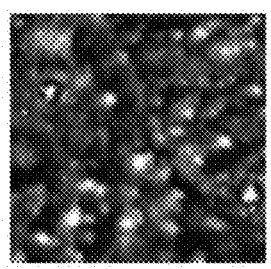
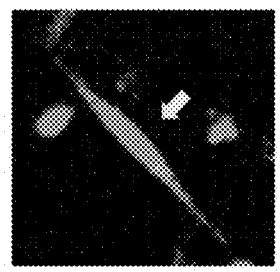
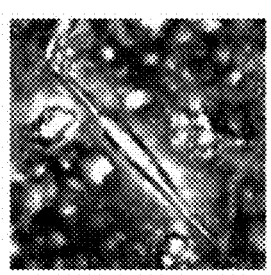
FIG.14B  FIG.14C FIGURE 15A – 15B
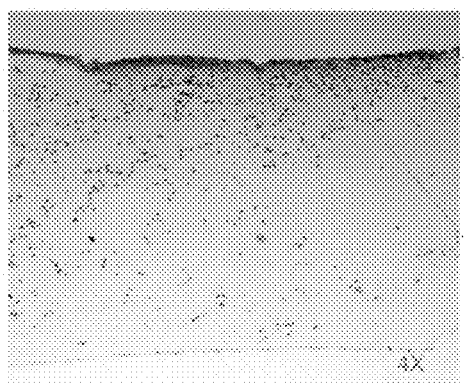 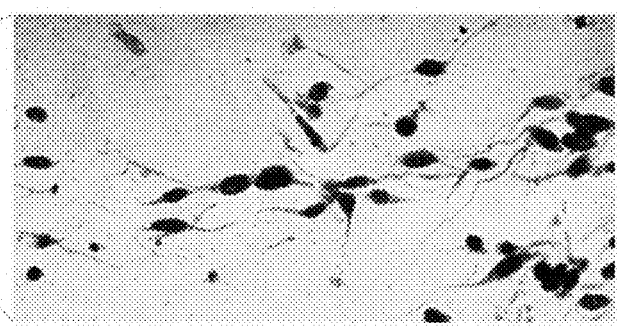
FIG.15A	FIG.15B FIGURE 16A – 16B
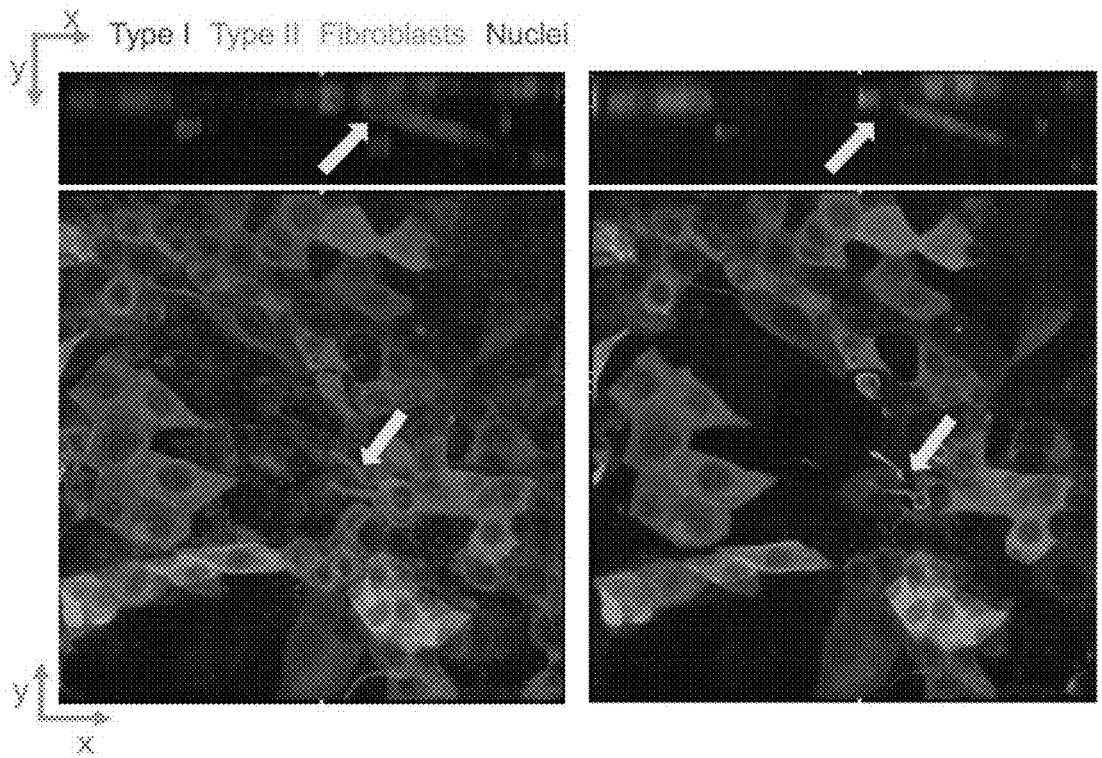
FIG.16A
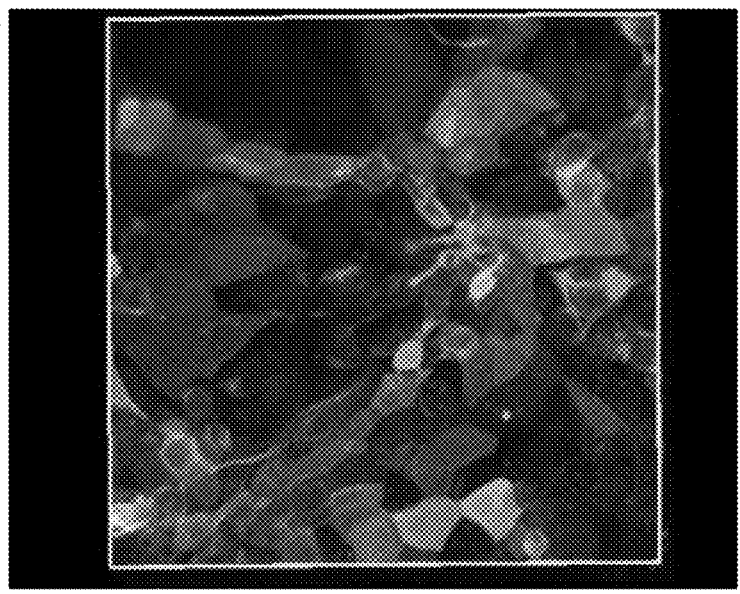
FIG.16B FIGURE 18A - 18E
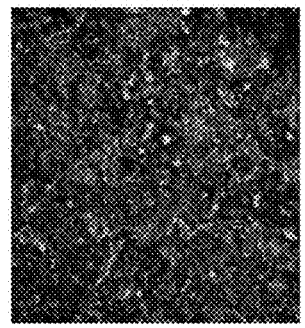
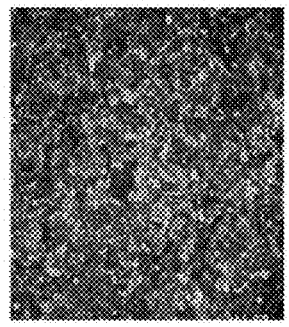
FIG.18A  FIG.18C
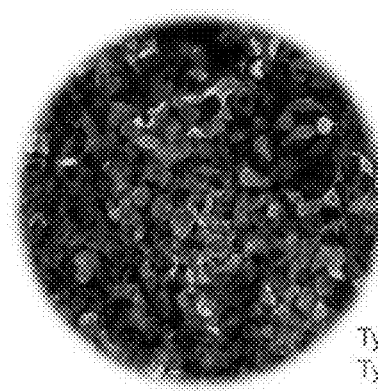
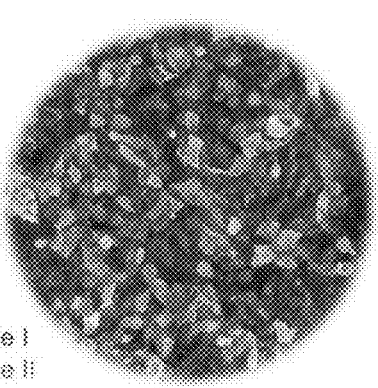
FIG.18B  FIG.18D
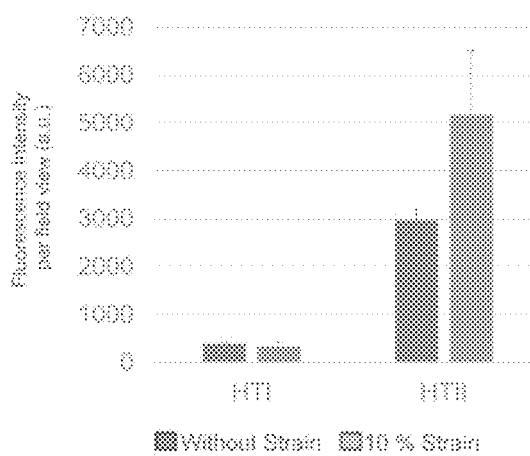
FIG.18E FIGURE 19A – 19B
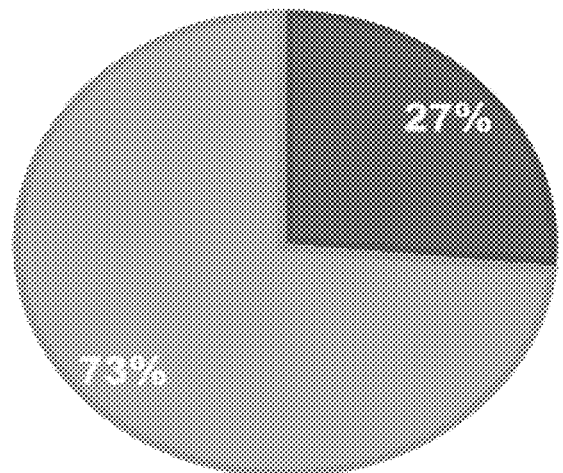
FIG.19A
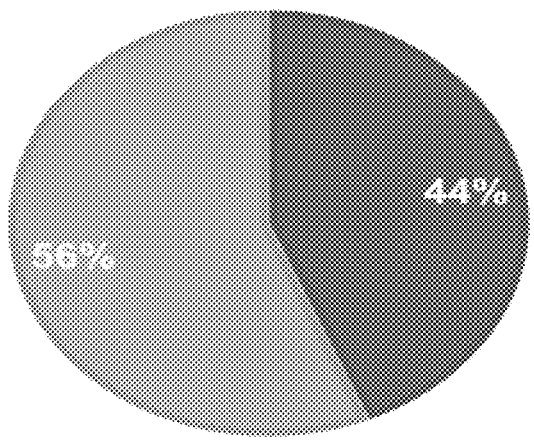
FIG.19B FIGURE 21A – 21D
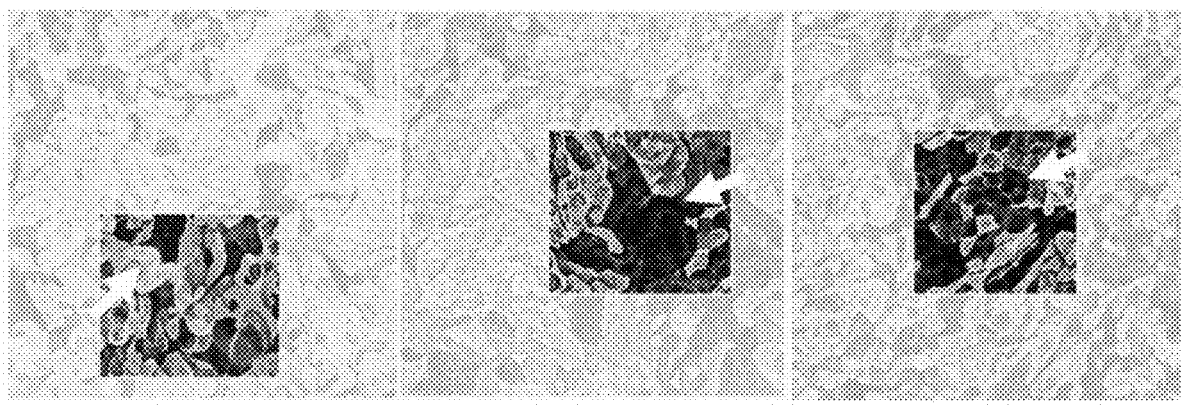
FIG.21A     FIG.21B     FIG.21C
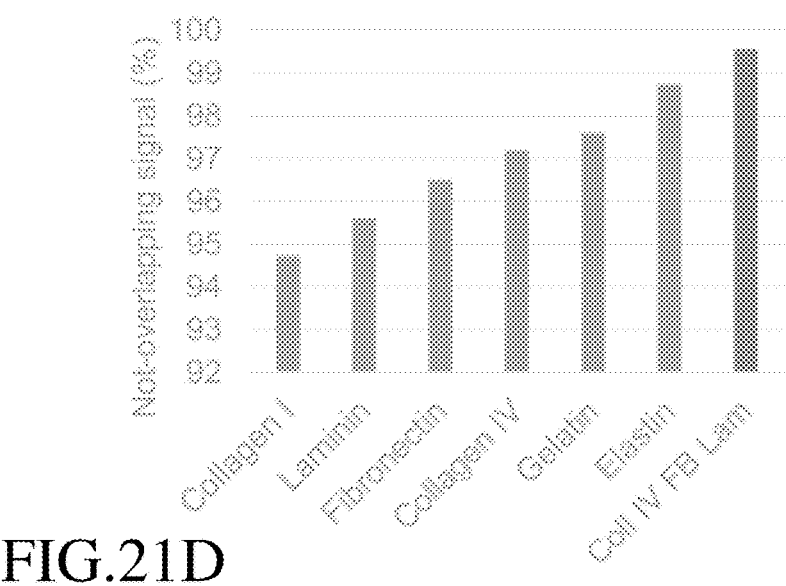
FIG.21D FIGURE 22A – 22B
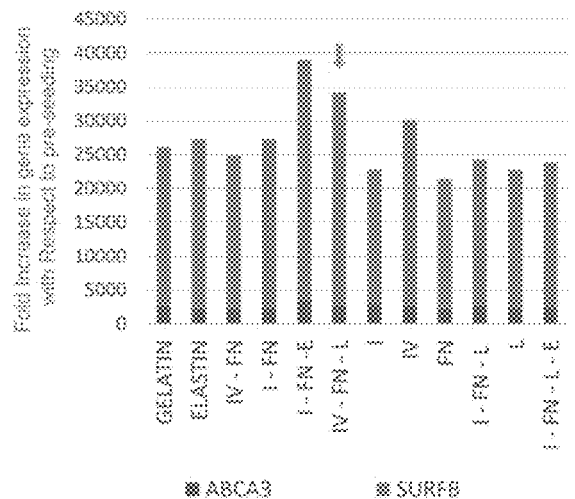
FIG.22A
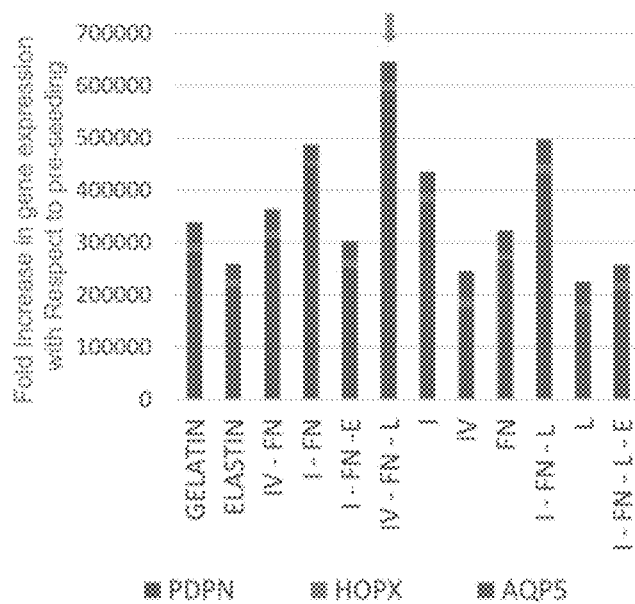
FIG.22B FIGURE 23A – 23C
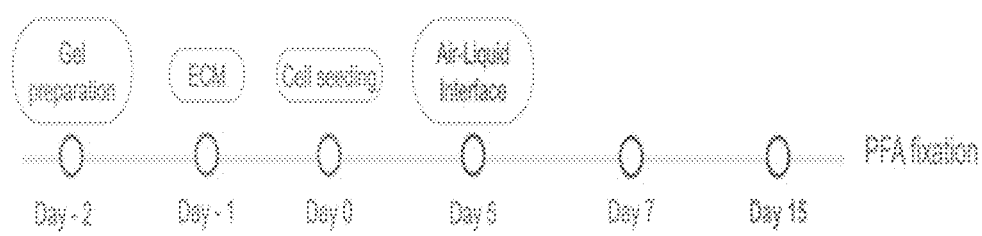
FIG.23A
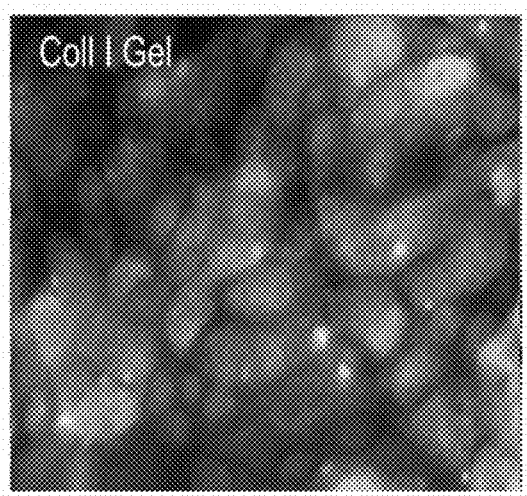
FIG.23B
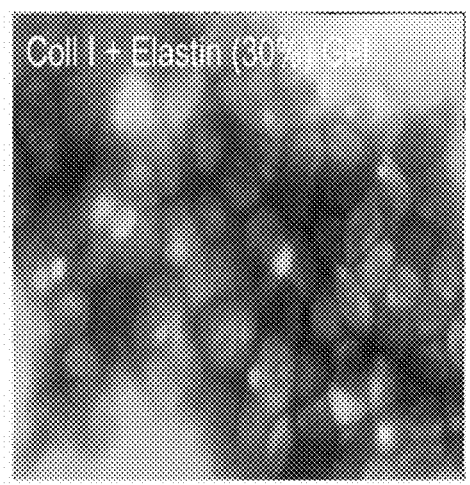
FIG.23C FIGURE 24A – 24H
FIG.24A          FIG.24B          FIG.24C          FIG.24D
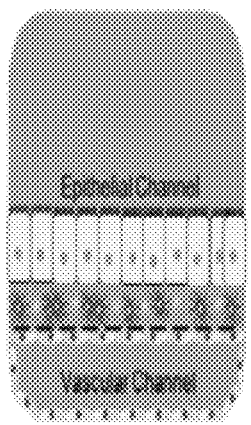 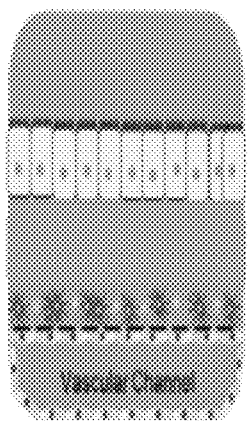 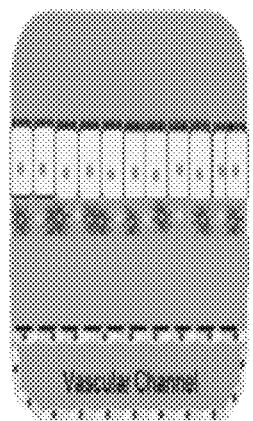 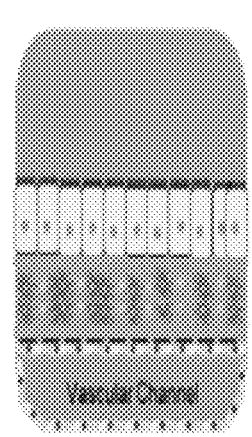
LPDCs under epis     LPDCs under gel     LPDCs over gel     LPDCs in gel
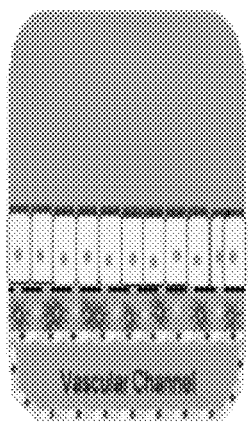 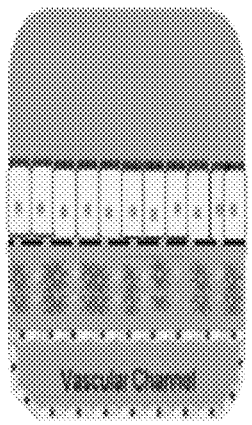 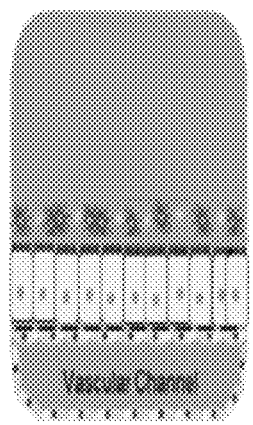
LPDCs in bottom channel   LPDCs in gel in bottom channel   LPDCs over epis
FIG.24E          FIG.24F          FIG.24G          FIG.24H
Legend:
- — — Membrane
- Gel
- — Endothelial Cells
- Epithelial Cells
- Lamina Propria

IN VITRO EPITHELIAL MODELS COMPRISING LAMINA PROPRIA-DERIVED CELLS

FIELD OF THE INVENTION

An in vitro microfluidic "organ-on-chip" is described herein that mimics the structure and at least one function of specific areas of the epithelial system in vivo. In particular, as multicellular, layered, microfluidic culture is described, allowing for interactions between lamina propria-derived cells and epithelial cells and endothelial cells. This in vitro microfluidic system can be used liar modeling inflammatory tissue, e.g. autoimmune disorders involving epithelia and diseases involving epithelial layers. These multicellular, layered microfluidic "organ-on-chip", e.g. "epithelia-on-chip" further allow for comparisons between types of epithelia tissues, e.g., lung (Lung-On-Chip), bronchial (Airway-On-Chip), skin (Skin-On-Chip), cervix (Cervix-On-Chip), blood brain barrier (BBB-On-Chip), etc., in additional to neurovascular tissue, (Brain-On-Chip), and between different disease states of tissue, i.e. healthy, pre-disease and diseased areas. Additionally, these microfluidic "organ-on-chips" allow identification of cells and cellular derived factors driving disease states in addition to drug testing for reducing inflammation effecting epithelial regions.

BACKGROUND

In vitro tissue model systems include cell lines, primary cell explant cultures and three-dimensional primary cell organoid culture systems. However, these models have significant limitations. Explant cultures, which have organotypic properties such as complex 3-dimensional (3D) architecture and cellular heterogeneity are limited in part by their lack of reproducibility of growing conditions between laboratories and their short-term nature.

What is needed is a better in vitro platform liar tissue modeling and drug testing, specifically in combination with modeling organs, in particular in relation to inflammatory diseases.

SUMMARY OF THE INVENTION

An in vitro microfluidic "organ-on-chip" is described herein that mimics the structure and at least one function of specific areas of the epithelial system in vivo. In particular, a multicellular, layered, microfluidic culture is described, allowing for interactions between lamina propria-derived cells and epithelial cells and endothelial cells. This in vitro microfluidic system can be used for modeling inflammatory tissue, e.g., autoimmune disorders involving epithelia. and diseases involving epithelial layers. These multicellular, layered microfluidic "organ-on-chip", "epithelia-on-chip" further allow for comparisons between types of epithelia tissues, e.g., lung (Lung-On-Chip), bronchial (Airway-On-Chip), skin (Skin-On-Chip), cervix (Cervix-On-Chip), etc., and between different disease states of tissue, i.e. healthy, pre-disease and diseased areas. Additionally, these microfluidic "organ-on-chips" allow identification of cells and cellular derived factors driving disease states in addition to drug testing for reducing inflammation effecting epithelial regions.

Additional types of microfluidic chips are contemplated, including but not limited to vaginal (e.g. Vagina-On-Chip), eye (e.g. Cornea-On-Chip; Retina-On-Chip), blood-brain bather (BBB; e.g. BBB-On-Chip), brain (e.g. Brain-On-Chip, including but not limited to neurovascular components, microglia, etc.); gall bladder (Gall Bladder-On-Chip), etc.

The present invention provides a fluidic device comprising: a) a first fluidic channel in contact with a semi-permeable membrane; is) first cells comprising at least one parenchymal cell type; and c) second cells comprising at least one stromal cell type. In one embodiment, said parenchymal cell type is selected from the group consisting of epithelial cells of the lung, epithelial cells of the skin and epithelial cells of the urogenital tract, in one embodiment, said epithelial cells of the lung are selected from the group consisting of alveolar epithelial cells and airway epithelial cells. In one embodiment, said epithelial cells of the skin comprise keratinocytes. In one embodiment, said parenchymal cell type is selected from the group consisting of hepatocytes, muscle cells, neurons and parenchymal cells of the pancreas. It is not meant to limit the type of parenchymal cell. Indeed, parenchymal cells may further include but are not limited to cells from kidney, endocrine organs, bone marrow, spleen, thymus, lymph node, etc.

In one embodiment, said muscle cells are selected from the group consisting of skeletal muscle cells, smooth muscle cells and cardiamyocytes. In one embodiment, at least one of said first cells and second cells comprise cancer cells. In one embodiment, at least one of said first cells and second cells comprise cells derived from a tumor. In one embodiment, at least one of said first cells and second cells comprise cells derived from a region in or around a tumor. In one embodiment, at least one of said first cells and second cells comprise cells derived from an ulcer. In one embodiment, at least one of said first cells and second cells comprise cells from a region of inflammation. In one embodiment, said stromal cell type is a lamina propria-derived cell. In one embodiment, said stromal cell type comprises resident immune cells. In one embodiment, said stromal cell type comprises cells selected from the group consisting of fibroblasts, macrophages, dendritic cells. Intraepithelial Lymphocytes (ILCs), resident T cells and resident B cells, etc. In one embodiment, said stromal cell types comprise primary stromal cells. In one embodiment, said primary stromal cells comprise biopsy-derived cells or lavage derived cells. In one embodiment, said primary stromal cells are patient-derived cells. In one embodiment, said patient-derived cells are from a patient with an inflammatory; disease. In one embodiment, said patient-derived cells are from a patient with cancer. In one embodiment, said patient-derived cells are from a patient with degenerative disease. The present invention is not meant to limit the variety of patient-derived cells and is not meant to be limited to a particular disease. Indeed, patient-derived cells may be obtained from patients with diseases including but not limited to genetic diseases, acquired diseases, etc. In one embodiment, at least a portion of said second cells are disposed in contact with said semi-permeable membrane. In one embodiment, the device further comprises a gel. In one embodiment, at least a portion of said second cells are disposed within said gel. In one embodiment, the device is a microfluidic device said first channel comprises a first microfluidic channel. In one embodiment, said microfluidic device further comprises a second microfluidic channel in fluidic communication with said first microfluidic channel. In one embodiment, said membrane is disposed between said first and second microfluidic channels. In one embodiment, said membrane is a porous membrane. In one embodiment, said device further comprises a removable top. in one embodiment, said device further comprises an open region in contact with at least one of said first fluidic channel, said semi-permeable membrane, said first cells, or said second cells. In one embodiment, said gel is fluid permeable. In one embodiment, said gel is water impermeable.

The present invention provides a method comprising a) providing a first fluidic device comprising, i) a first fluidic channel in contact with a semi-permeable membrane, ii) first cells comprising at least one parenchymal cell type, and iii) second cells comprising at least one stromal cell type; and b) perfusing said first fluidic device with fluid. In one embodiment, said parenchymal cell type is selected from the group consisting of epithelial cells of the lung, epithelial cells of the skin and epithelial cells of the urogenital tract. In one embodiment, said epithelial cells of the lung are selected from the group consisting of alveolar epithelial cells and airway epithelial cells. In one embodiment, said epithelial cells of the skin comprise keratinocytes. in one embodiment, said parenchymal cell type is selected from the group consisting of hepatocytes, muscle cells, neurons and parenchymal cells of the pancreas, in one embodiment, said muscle cells are selected from the group consisting of skeletal muscle cells, smooth muscle cells and cardiomyocytes. In one embodiment, at least one of said first cells and second cells comprise cancer cells. In one embodiment, at least one of said first cells and second cells comprise cells derived from a tumor, in one embodiment, at least one of said first cells and second cells comprise cells derived from a region in or around a tumor. In one embodiment, at least one of said first cells and second cells comprise cells derived from an ulcer. In one embodiment, at least one of said first cells and second cells comprise cells derived from a wound. In one embodiment, at least one of said first cells and second cells comprise cells derived from a granuloma. In one embodiment, at least one of said first cells and second cells comprise cells derived from a hyperplastic lesion. In one embodiment, at least one of said first cells and second cells comprise cells from a region of inflammation. In one embodiment, said stromal cell type is a lamina propria-derived cell, in one embodiment, said stromal cell type comprises resident immune cells, in one embodiment, said stromal cell type comprises cells selected from the group consisting of fibroblasts, macrophages, and dendritic cells. In one embodiment, said stromal cell type comprises primary stromal cells. In one embodiment, said primary stromal cells comprise biopsy-derived cells or lavage-derived cells. In one embodiment, said primary cells are patient-derived cells. In one embodiment, said patient-derived cells are from a patient with an inflammatory disease. In one embodiment, at least a portion of said second cells are disposed in contact with said semi-permeable membrane. In one embodiment, the device further comprises a gel. In one embodiment, at least a portion of said second cells are disposed within said gel, in one embodiment, the device is a microfluidic device, said first channel comprises a first microfluidic channel. In one embodiment, said microfluidic device further comprises a second microfluidic channel in fluidic communication with said first microfluidic channel. In one embodiment, said membrane is disposed between said first and second microfluidic channels. In one embodiment, said membrane is a porous membrane, in one embodiment, said gel is fluid permeable. In one embodiment, said gel is water impermeable. In one embodiment, said device further comprises a removable top. In one embodiment, said method further comprises c) removing said removable top. In one embodiment, said device further comprises an open region in contact with at least one of said first fluidic channel, said semi-permeable membrane, said first cells, or said second cells. in one embodiment, said method further comprises c) contacting said first cells, said second cells or both with a first agent in one embodiment, said method further comprises d) detecting at least one response to said first agent. In one embodiment, said at least one response comprises modulation of the inflammation reaction. In one embodiment, the said at least one response comprises modulation of cytokine profile, in one embodiment, the said at least one response comprises modulation of a proinflammatory factor. In one embodiment, the said at least one response comprises modulation of a proinflammatory factor profile. In one embodiment, the said at least one response comprises modulation of other inflammatory factors. In one embodiment, said at least one response comprises modulation of gene expression, in one embodiment, said at least one response comprises modulation of cell or tissue morphology. In one embodiment, said first agent causes an inflammatory reaction. In one embodiment, the method further comprises d) contacting said first cells, said second cells or both with a second agent. In one embodiment, the method further comprises e) detecting inhibition of said inflammatory reaction by said second agent. The present invention encompasses a variety of responses and is not meant to limit the response of cells or the types of detection of these responses. Therefore, it is not meant to limit the type of detecting, Indeed, in one embodiment, said method further comprises detecting a proliferative reaction, a fibrotic process, inhibition of degeneration, inhibition of proliferation, a proliferative reaction, inhibition of a proliferative reaction, induction of fibrosis, inhibition of fibrotic process, promoting degeneration, inhibiting degenerative processes or pathways, etc. In one embodiment, the method further comprises f) comparing the degree of inhibition by said second agent with said second cells of a first patient with the degree of inhibition by said second agent with second cells of a second patient. In one embodiment, the method further comprises f) comparing the degree of inhibition by said second agent with said second cells of a first organ with the degree of inhibition by said second agent with second cells of a second organ. In one embodiment, the method further comprises f comparing the degree of inhibition by said second agent with said second cells of a first region of an organ with the degree of inhibition by said second agent with second cells of a second region of an organ.

The present invention provides a method comprising: a) providing a first and second fluidic devices, each device comprising: i) a first fluidic channel in contact with a semi-permeable membrane, ii) parenchymal cells, and iii) stromal cells, wherein said parenchymal cells, said first stromal cells or both cells of said first fluidic device are different from said parenchymal cells, said first stromal cells or both cells of said second device; and b) perfusing said first and second fluidic devices with fluid. in one embodiment, said parenchymal cells, said first stromal cells or both cells of said first fluidic device are derived from a different organ than said parenchymal cells, said first stromal cells or both cells from said second fluidic device, in one embodiment, said parenchymal cells, said first stromal cells or both cells of said first fluidic device are derived from the same organ than said parenchymal cells, said first stromal cells or both cells from said second fluidic device. In one embodiment, said parenchymal cells, said first stromal cells or both cells of said first fluidic device come from a first region associated with a first phenotype and said parenchymal cells, said first stromal cells or both cells from said second fluidic device come from a second region associated with a second phenotype. In one embodiment, said first phenotype is a diseased phenotype and said second phenotype is a healthy phenotype. In one embodiment, said first phenotype is an inflamed phenotype and said second phenotype is a non-inflamed phenotype. In one embodiment, said first phenotype is a cancer phenotype and said second phenotype is a non-cancer phenotype. In one embodiment, said first and second regions are from the same organ, hi one embodiment, said first and second regions are from the same patient. In one embodiment, the method further comprises c) comparing at least one property of at least one cell type of said first fluidic device with at least one cell type of said second fluidic device, hi one embodiment, said property comprises permeability. In one embodiment, said property comprises cytokine secretion. In one embodiment, said property comprises gene expression, in one embodiment, said property comprises cell morphology. In one embodiment, said property comprises cell-cell interactions, hi. one embodiment, said property comprises cell viability. In one embodiment, said property comprises cell apoptosis. In one embodiment, said property is selected from the group consisting of protein expression, protein activity, extent of post-translational modification, and combinations thereof in one embodiment, said first fluidic device, said second fluidic device or both are perfused with an agent. In one embodiment, both fluidic devices are perfused with the same agent, in one embodiment, said agent is at a first concentration for said first device and a second concentration for said second device. In one embodiment, said fluidic devices are perfused with different agents. In one embodiment, only the first fluidic device is perfused with said agent. In one embodiment, said parenchymal cells are selected from the group consisting of epithelial cells of the lung, epithelial cells of the skin and epithelial cells of the urogenital tract. In one embodiment, said epithelial cells of the lung are selected from the group consisting of alveolar epithelial cells and airway epithelia/cells. In one embodiment, said epithelial cells of the skin comprise keratinocytes. In one embodiment, said parenchymal cell type is selected from the group consisting of hepatocytes, muscle cells, neurons and parenchymal cells of the pancreas. In one embodiment, said muscle cells are selected from the group consisting of skeletal muscle cells, smooth muscle cells and cardiomyocytes. In one embodiment, at least one of said first and second fluidic devices comprise cancer cells. In one embodiment, at least one of said first and second fluidic devices comprise cells derived from a tumor. In one embodiment, at least one of said first and second fluidic devices comprise cells derived from a region in or around a tumor. In one embodiment, at least one of said first and second devices comprise cells derived from an ulcer. in one embodiment, at least one of said first and second fluidic devices comprise cells from a region of inflammation. In one embodiment, said stromal cells comprise lamina propria-derived cells, in one embodiment, said stromal cells comprises resident immune cells. In one embodiment, said stromal cells comprises cells selected from the group consisting of fibroblasts, macrophages, and dendritic dells. In one embodiment, said stromal cells comprises primary stromal cells. In one embodiment, said primary stromal cells comprise biopsy-derived cells or lavage-derived cells. in one embodiment, said primary cells are patient-derived cells. In one embodiment, said patient-derived cells are from a patient with an inflammatory disease. In one embodiment, at least a portion of said cells in said first and second fluidic devices are disposed in contact with said semi-permeable membrane. In one embodiment, at least one of said first and second fluidic devices further comprises a gel. In one embodiment, at least a portion of said parenchymal cells or said stromal cells or both are disposed within said gel. In one embodiment, the first and second fluidic devices are microfluidic devices, said first channel comprising a first microfluidic channel, in one embodiment, said microfluidic device further comprises a second microfluidic channel in fluidic communication with said first microfluidic channel. In one embodiment, said membrane is disposed between said first and second microfluidic channels. In one embodiment, said membrane is a porous membrane. In one embodiment, said gel is fluid permeable. In one embodiment, said gel is water impermeable. In one embodiment, said device farther comprises a removable top. In one embodiment, said method further comprises c) removing said removable top. In one embodiment, said device further comprises an open region in contact with at least one of said first fluidic channel, said semi-permeable membrane, said parenchymal cells, or said stromal cells or both.

The present invention contemplates combining features from different embodiments. The present invention contemplates removing features from the above-indicated embodiments. For a non-limiting example, co-cultures of epithelial cells with endothelial cells and lamina propria-derived cells may have a feature removed. For example, subsets of cells isolated from lamina propria may be removed from the configuration in order to identify subsets of LP-derived cells contributing to specific disease phenotypes. As one example, lung fibroblast cells may be isolated from LP derived cells for identifying contributions to altering configuration of the epithelial layer during co-cultures on-chip with epithelium. The present invention contemplates adding features to the configuration in order to identify LP-cells initiating chances in configuration of epithelial layers, e.g. adding elastin to microfluidic devices containing pre-disease, diseased or healthy alveolar cells. The present invention contemplates substituting features in the above-indicated embodiments. For a non-limiting example, lung fibroblasts from commercial sources may be substituted with lung fibroblasts isolated directly from humans.

Definitions

The terms, "Organ-On-Chip" and the like, i.e., "-On-Chip" or "chip" refers to a "microfluidic device" for modeling any one or more types of tissue, including but not limited to the lung, airway, skin, etc. An "Organ-On-Chip" device is not limited to modeling any particular organ. In fact, "Organ-On-Chip" refers to a "microfluidic device" for modeling any one or more subtypes of airway tissue, skin brain etc, including but not limited to the blood brain harder, skin, etc.

As used herein, "fluid" refers to a substance that has no fixed shape and yields easily to external pressure; e.g. a gas or a liquid. "Fluidity" of a substance refers to a capability to flow. As opposed to "viscosity" in reference to a fluid, referring to a measure of a resistance to flowing, for example, honey has a much higher viscosity than water.

As used herein, a "fluidic device" refers to a capable of having defined manipulation of the working fluid by active components. For example, a "microfluidic device" includes such components as micropumps, microvalves, etc.

As used herein, "microfluidic" relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction.

In some instances the geometry of a microfluidic channel may be configured to control the fluid flow rate through the channel (e.g. increase channel height to reduce shear). Microfluidic channels can be formed of various geometries to facilitate a wide range of flow rates through the channels.

As used herein, "channels" are pathways (whether straight, curved, single, multiple, in a network, etc.) through a medium (e.g. silicon) that allow for movement of liquids and gasses. Channels thus can connect other components, i.e., keep components "in communication" and more particularly, "in fluidic communication" and still more particularly, "in liquid communication," Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even through they are not in direct contact with each other. For example, two components may be coupled to each other through an intermediate component (e.g. tubing or other conduit).

As used herein, "fluidically connected" refers to two or more components connected in an appropriate manner such that a fluid or at least a portion of a fluid can directly or indirectly pass or flow from one component to a second component. Without limitations, two or more components can be fluidically connected together, for example, using one or more fluid-transfer connecting means (e.g., adaptors, tubing, splitters, valves, and/or channels) between the two or more components. For example, two or more components can be fluidically connected by connecting an outlet of one component to an inlet of another component using tubing, a conduit, a channel, piping or any combinations thereof. In other embodiments, two or more components can be fluidically connected together with one or more other connecting means (e.g., devices, systems, and/or modules that can perform an additional function other than fluid transfer, e.g., but not limited to, trapping air bubbles, filtration, signal detection, and/or imaging) are present between the two or more components.

As used herein, "removable top" refers to a cover that is capable of being removed from a device preferably without using screws (or the like) and that is not a molded part of a device.

As used herein, "perfusing" in relation to a fluidic device refers to introducing fluid into the device. As an example of perfusing a device containing cells, perfusing the device is supplying or treating cells or tissues with a fluid. As an example, fluid flowing through a fluidic device in contact with cells is also referred to as perfusing.

As used herein, "membrane" generally refers to a layer capable of blocking solute particles. Examples of membranes include but are not limited to a semi-permeable membrane, a porous membrane, etc.

As used heroin, the term "porous" generally refers to a material that is permeable or selectively permeable. The term "permeable" as used herein means a material that permits passage of a fluid (e.g., liquid or gas), a molecule, and/or a whole living cell. The term "selectively permeable" as used herein refers to a material that permits passage of one or more target group or species, but acts as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In accordance with some embodiments of the invention, a selectively-permeable membrane can allow certain cell types to pass therethrough but not other cell types.

As used herein, "cell" refers to any eukaryotic or prokaryotic cell (e.g., bacterial cells such as bacteria (e.g. *E. coli*), fungal, (e.g. yeast), mammalian cells, avian cells, amphibian cells, plant cells, fish cells, and insect cells). In general, prokaryotic cells are those that do not have a membrane-bound nucleus while eukaryotic cells have a "true" nucleus containing their DNA. Eukaryote includes both unicellular and multicellular organisms. Examples of mammalian cells include but are not limited to parenchymal cell types, e, g, epithelial cells of the lung, epithelial cells of the skin and epithelial cells of the urogenital tract.

As used herein, "cell type" refers to a classification used to include morphologically or phenotypically similar cells.

As used herein, "resident" in reference to cells, i.e. "resident cells" refers to cells isolated from, or descriptively found in, specific tissues of the body. For example, resident cells may be isolated from tissue biopsies, such as skin, or specific parts of biopsies, such as the epidermis and/or dermis of skin, wherein leukocytes, monocytes, fibroblasts, etc., contained in the biopsy are isolated for use, i.e. "resident cells" or "resident-derived cells". Such resident cells may be used in chips described herein as primary or cultured cells. Additionally, representatives of resident cells may be used, such as cell lines or cells isolated from other types of tissues, i.e. fibroblast cells lines, keratinocyte cell lines, e.g. immortalized or cancerous, i.e. capable of numerous passages, including cells for specific cell types derived from induced pluripotent stem cells (also known as human iPS cells or human iPSCs), human embryonic stem cells (hES cells). etc.).

As used herein, "lamina propria" refers to a layer of loose connective tissue, which lies beneath the epithelium in the body (such as the respiratory tract (airway), skin etc.). "Lamina propria" fills in the space between the suhepithelial basement membrane complex (a layer present in vivo underneath epithelial cells) to the muscularis mucosae layer.

As used herein, "lamina propria-derived cells" and "LP-derived cells" and "LPDCs" refer to cells isolated from lamina propria, e.g. resident immune cells, fibroblasts, macrophages, dendritic stromal cells, etc., including primary cells, e.g. patient-derived cells, i.e. a patient with an inflammatory disease, and cultured cells, e.g. lamina propria-derived cells cultured over time prior to use. LPDCs also refers to cells used in the context of specific tissues (e.g. mucosal tissues), thus in one embodiment, LP-derived cells are isolated from specific tissues (e.g. mucosal tissues), LP-derived cells are not limited to mucosal tissues, as they may be isolated from tissues extending into mucosal areas, for example, cells in stromal areas or submucosal regions, LP-derived cells may be used directly after isolation or under go culture to expand cell numbers prior to use. LP-derived cells may undergo isolation techniques before or after culturing or freezing. In other embodiments, LP-derived cells may be cryopreserved (frozen) prior to use.

As used herein, "parenchyma" refers in general to functional cells or parts of an organ that may also be referred to descriptively as "parenchymal", As one example, in brain tissue, "parenchyma" refers to the functional tissue comprising at least two types of "parenchyma cells", i.e. brain cells, e.g. neurons and glial cells. As another example, parenchyma cells of the lung or "lung parenchma" refers to lung tissue outside of the circulation system involved with gas exchange, including but not limited to alveoli and respiratory bronchioles (i.e. small bronchial tubes leading to and inside of alveolar sacs). As yet another example, in cancer, parenchyma refers to the cancerous cells and/or cancer tissue (i.e. tumor). in yet another example, "epithelial tissue" and "epithelial cells" are considered parenchyma, e.g. epithelial cells of the lung including but not limited to alveolar epithelial cells, airway epithelial cells, etc., epithelial cells of the skin including. but not limited to keratinocytes.

In contrast, as used herein, the terms "stromal" and "stroma" refers in general to structural (i.e. supportive) tissue, i.e. stromal tissue" of organs, e.g. connective tissues, including but not limited to ECM, blood vessels, nerves, ducts, for supporting parenchyma cells i.e. nutritionally, immunologically, etc, or providing a frame for holding together parenchyma cells as an organ. Stromal cells, including cells capable of secreting connective tissue, e.g. collagen, elastin, reticular fibers, etc., include but not limited to, for examples, bone marrow derived mesenchymal stem cells, fibroblasts, myofibroblasts, mural cells (pericytes) of the vasculature, etc. Such cells may be found ire or near sites of inflammation, such as in or near the lamina propria in vivo, e.g. mucosa, submucosa, etc. and may also include "multipotent stromal cells" or "mesenchymal stromal cells" or "MSCs" found in both in the mucosal region, e.g. in lamina propria-derived cell populations and in submucosal regions, etc. In some embodiments, stromal cells are contemplated for use in microfluidic devices of the present inventions. In some embodiments, "stromal cells" are contemplated for use after isolation from lamina propria derived cells. in some embodiments, stromal cells are contemplated for use derived from regions that do not include lamina propria. in some embodiments, stromal cells are contemplated for use that are a mixture of LP-derived and non-LP-derived cells, e.g. when biopsy tissue used for isolating cells includes both mucosa and submucosal cells. In some embodiments, stromal cells are isolated from healthy and diseased and/or from different sites within the same individual. For example, stromal cells may be derived from (e.g. isolated from) an in vivo site of cancer vs. derived from an in vivo healthy looking site, or from a cultured cell line.

As used herein, "airway" refers in general to the bronchial system, e.g. lined with bronchial. epithelial cells.

As used herein, the term "culture" refers to a composition, whether liquid, gel, or solid, which contains one or more microorganisms and/or one or more cells.

As used herein, "cell culture" refers to any in vitro culture of cells. included within this term are continuous cell lines (e.g., with an immortal phenotype), primary cell cultures, transformed cell lines, finite cell lines (e, g, non-transformed cells), and any other cell population maintained in vitro.

As used herein, "culture media" and "cell culture media" refer to media that are suitable to support maintenance and/or growth of cells in vitro (i.e., cell cultures). Cultured cells include primary cultured cells and cell lines.

As used herein, "gel" refers to a jelly-like substance and the process of solidifying a solution of gel particles into a gel, e.g., to form a gel. A gel is typically fluid permeable, e.g. water impermeable.

As used herein, "microorganism" refers to any organism of microscopic or ultramicroscopic size including, but not limited to, viruses, bacteria, and protozoa.

A "primary cell" refers to a cell that is directly obtained from a tissue or organ of an animal whether or not the cell is in culture.

A "cultured cell refers to a cell which has been maintained and/or propagated in vitro.

As used herein, "morphology" in reference to a cell refers to a visual form of a cell, such as a cell that appears to have a migratory morphology or morphologic form, e.g. elongated or flat cell shape, i.e. a macrophage, vs. a cell that appears to be non-migratory, e.g. having a rounded cell shape, i.e. a monocyte.

As used herein, "phenotype" refers to observable characteristics of an individual resulting from the interaction of its genotype with the environment, including but not limited to a disease phenotype, a healthy phenotype. A phenotype may refer to "inflamed" tissue or "non-inflamed" tissue.

As used herein, "agent" or "compound" refers to a substance and preferably a test substance, such as a drug, cytokine, etc.

As used herein, the term "biopsy" refers to a sample of the tissue that is removed from a body, either as a solid or fluid (in liquid form, such as by lavaging or rinsing out cells, e.g. a respiratory bronchoalveolar lavage or lung sample, or as a blood sample) for obtaining biopsy-derived cells or lavage-derived cells, respectively.

As used herein, the term "irritant" refers to a stimulus or agent that induces the state of irritation in an epithelial lining, for example, a bacterial toxin or an allergen. that causes activation of resident mononuclear white blood cells, leukocytes, lymphocytes, etc, in the lamina propria (in vivo), lamina propria-derived cells (in vitro), or actual damage to epithelial cells, in vivo or in vitro, that in turn triggers activation of resident immune cells any of which may induce irritation.

As used herein, the term "irritation" refers to initiation of inflammation. By way of example only, this may be due to an allergy or damage to epithelial cells in the lining of the respiratory system.

As used herein, the term "inflammation" refers to an in vivo physical condition in which a part of tissue in a body may become reddened, swollen (enlarged), or damaged (ulcerated) especially as a reaction to injury or an irritant. Areas of inflammation can have increased blood flow and capillary permeability, i.e. changes in endothelial cells lining capillaries resulting in capillary dilation and leukocyte infiltration into the irritated and/or inflamed tissues, along with activated. immune cells, including white blood cells, leukocytes, lymphocytes, etc., including substances produced by activated immune cells. Inflammation may occur suddenly (acute) or gradually over time (chronic). Inflammation may be local, i.e. in one location as a "patch" or "spot" or may be in several areas as numerous patches, including ulcers, or contiguous involving a large area of tissue. Inflammation may be limited to epithelial regions and underlying lamina propria (for example, mucosal areas), or may extend to the submucosa, or extend to the muscularis propria and may further extent to the outermost layer, adventitia, in contact with other parts of the body. Inflammation may also refer to a physiological condition in vitro, as described herein; where lamina propria-derived cells are isolated from inflammatory or pre-inflammatory tissue, such that resident immune cells may be preactivated or activated.

BRIEF DESCRIPTION OF THE DRAWINGS

FIGS. 4A-C Show an exemplary schematic of one embodiment a 3D Alveolus Lung Ort-Chip demonstrating locations of ports and input channels leading into the main growing chamber in relation to cell layers, FIG. 4A Overview of Epithelial surface (upper channel) showing exemplary primary adult human alveolar epithelial cells seeded on ECM made of Collagen IV, Fibronectin and Laminin. FIG. 4B Overview of Vascular compartment (lower channel) showing exemplary primary adult microvascular endothelial cells are seeded on ECM made of Collagen IV and Fibronectin, FIG. 4C An expanded side view of Tridimensional stroma showing exemplary primary adult human fibroblasts embedded within the stromal compartment.

FIG. 6A shows an exemplary schematic of an open top chip with an exemplary micrograph of stained cells within the central chamber, FIG. 6B shows an enlarged view of the exemplary micrograph showing stained (red) Type I-Like pneumocytes co-stained for Actin (green); Nuclei (blue).

FIGS. 8A-B Show exemplary micrographs demonstrating the detection of Type I and Type II Pneumocytes, HTI-56 Type I (red); HTII-280—Type II (green) and DAPI stained Nuclei (blue). FIG. 8A shows a co-stained area on-chip while the micrographs in FIG. 8B shows enlarged micrographs, using different filters, of the area outlined in white dotted line in FIG. 8A. Upper, micrograph showing both cell types in relation to nuclei; middle, micrograph showing Type I cells (red) in relation to nuclei; and lower, micrograph showing Type II cells (green) in relation to nuclei.

FIGS. 9A-B Show exemplary micrographs further demonstrating the presence of Type I-like and Type II pneumocytes on-chip using specific cellular markers, e.g. FIG. 9A pneumocyte Markers Mature Surfactant C Type II (green) and FIG. 9B Podoplanin Type I (red) in relation to nuclei (blue).

FIGS. 10A-C Show exemplary micrographs further demonstrating the presence of E-Cadherin and Na/K-pump proteins at 15 days post seeding. FIG. 10A An exemplary micrograph showing triple stained cells on-chip: Na+/K+-pump (red) E Cadherin (green) Nuclei (blue). FIG. 10B An exemplary micrograph showing N pump (red). FIG. 10C An exemplary micrograph showing E-Cadherin (green).

FIGS. 12A-B Show exemplary micrographs demonstrating the presence of Connexin 43—Gap Junction, Connexin 43 (grey); Nuclei (blue), FIG. 12A shows co-stained cells. FIG. 12A-B Shows Connexin 43 (grey) staining where yellow arrows point to individual cells.

FIG. 13A lung fibroblasts stained for Phalloidin (pink) and Nuclei (blue). FIG. 13B Phalloidin (pink) and Type I-Like cells (green). White Bar=100 um.

FIGS. 14A-C Show exemplary micrographs demonstrating assessment of Fibroblast Viability growing on-chip, FIG. 14A Maximum intensity projection of Z-tack. FIG. 14B Live Dead. FIG. 14C Phase Contrast (left) Phase Contrast Merge with Live Dead. Live dead staining shows high percentage of cell surviving on chip on day 15 post-seeding. Dead fibroblasts: rounded morphology and red nuclei. Live fibroblasts: typical elongated morphology and green cytoplasm.

FIGS. 15A-B Show exemplary micrographs demonstrating Distribution and Morphology of Alveolar Fibroblasts On-Chip. Fibroblasts are mostly localized underneath the epithelial surface. FIG. 15A, and display typical stellate shape, FIG. 15B.

FIGS. 16A-B Shows exemplary micrographs demonstrating fibroblasts protrude towards the alveolar epithelium. FIG. 16A Type I (red) Type II (green) Fibroblasts (red) Nuclei (blue). FIG. 16B 3D animation.

FIGS. 18A-E Show exemplary micrographs demonstrating effect of mechanical strain on epithelial cells while FIG. 18E shows a graph comparing the expression of these markers on cells, with and without strain. FIGS. 18A/B Without strain, FIGS. 18C/D with 10% Strain, Stained Type cells are shown in red. Stained Type II cells are shown in green. FIG. 18E shows that strain increases expression of the HTII marker. Fluorescence Intensity per field view (a.u.) HTI vs. HTII.

FIGS. 19A-B Show exemplary graphs showing an exemplary effect of breathing motion on increasing expression of the Type II marker HT-II 280 vs. Type I markers. FIG. 19A No strain resulting in 27% vs. 73%, respectively; and FIG. 19B Membrane under strain resulting in 44% vs. 56%, respectively.

FIGS. 21A-D Show exemplary effects of different ECM Composition on Epithelial Cells. FIG. 21A-C shows HTI-56 (Type I-Like cells) (red) and HTII-280 (Type II cells) (green) exposed to FIG. 21A Coll I; FIG. 21B Coll IV; FIG. 21C Coll. IV—FN—L. FIG. 21D shows a graphical comparison markers demonstrating segregation of Type I-Like and Type II cell markers.

FIGS. 22A-B Show an exemplary gene expression of markers for FIG. 22A Type II Epithelial Cells and FIG. 22B Type I Epithelial Cells.

FIGS. 23A-C FIG. 23A Shows an exemplary schematic timeline for use with a paraformaldehyde (PEA) fixed cell based readout FIG. 23B Exemplary cell staining after growing on a Coll I Gel. FIG. 23C Exemplary cell staining after growing on a Coll Elastin (30%) Gel, Live cells (green), dead cells (debris) (red), nuclei (blue).

FIGS. 24A-G Show exemplary embodiments of epithelial channels and vascular channels, with or without a gel, in. a gut-on-chip with symbol information provided in FIG. 24H. FIG. 24A shows LPDCs located under Epithelial Cells, FIG. 24B shows LPDCs located under gel. FIG. 24C shows LPDCs located over gel. FIG. 24D shows LPDCs located in gel, FIG. 24E shows LPDCs located in bottom channel. FIG. 24F shows LPDCs located in gel in bottom channel. FIG. 24G shows LPDCs located over Epithelial Cells. FIG. 24H shows symbols representing; membrane, gel, endothelial cells, e.g. HUVEC, Epithelial. Cells (epis) and lamina Propria (LP) Derived Cells (LPDC).

GENERAL DESCRIPTION OF THE INVENTION

Figure 1A:
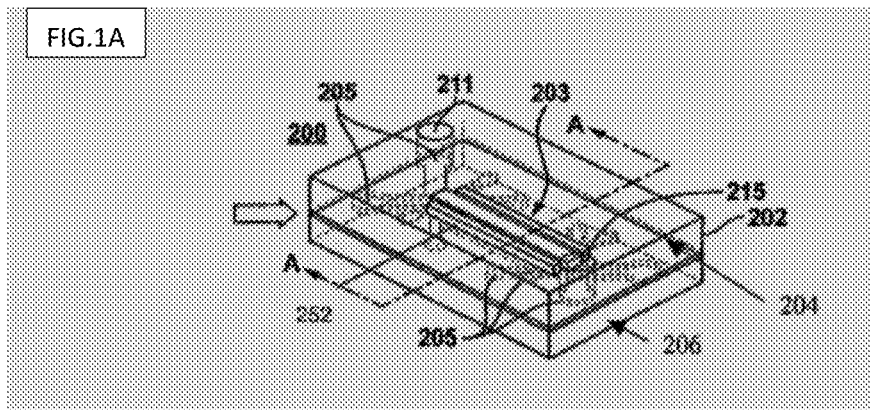
FIG. 1A Illustrates a perspective view of a microfluidic device with microfluidic channels in accordance with an embodiment.

An in vitro microfluidic "organ-on-chip" is described herein that mimics the structure and at least one function of specific areas of the epithelial system in vivo in particular, a multicellular, layered, microfluidic culture is described, allowing for interactions between lamina propria-derived cells and epithelial cells and endothelial cells. This in vitro microfluidic system can be used for modeling inflammatory tissue, autoimmune disorders involving epithelia and diseases involving epithelial layers. This microfluidic system may be used for modeling infectious disease. This microfluidic system may be used for modeling chronic inflammatory diseases. This microfluidic system may be used for modeling degenerative diseases. This microfluidic system may be used for modeling malignancies. These multicellular, layered microfluidic "organ-on-chip", e.g. "epithelia-on-chip" further allow for comparisons between types of epithelia tissues, e.g., lung (Lung-On-Chip), bronchial (Airway-On-Chip), skin (Skin-On-Chip), cervix (Cervix-On-Chip), blood brain barrier (BBB-On-Chip), etc., in additional to neurovascular tissue, (Brain-On-Chip), and between different disease states of tissue, i.e. healthy, pre-disease and diseased areas.

Additionally, these microfluidic "organ-on-chips" allow identification of cells and cellular derived factors driving disease states in addition to drug testing for reducing inflammation effecting epithelial regions.

I. Microfluidic "Organ-On-Chips" With Lamina Propria-Derived

The present invention contemplates methods and procedures for incorporating of lamina propria-derived cells (e.g. primary LPDC-derived, resident immune cells, etc.) microfluidic devices or "organs on chips" to model mucosal tissue microenvironments for a number of organ types including but not limited to the airway, lung, and skin. For example, in one embodiment, a Lung-On-Chip (microfluidic device) may comprise components such as: 1) alveolar epithelial cells (e.g. to model the lung epithelium 2) primary resident immune cells isolated from alveolar lamina propria, i.e. lamina propria-derived cells, 3) and vascular endothelial cells (e.g. HUVEC cells) to model the microvasculature of the alveolar sac. In another exemplary chip, Alveolus Lung-On-Chip, three lung tissue cell types: alveolar epithelial cells, fibroblasts and endothelial cells were incorporated into one embodiment of an Open-Top design. In one embodiment, the microfluidic device comprises top and bottom channels separated by a membrane. In some embodiments, the upper channel may simulate a gas-liquid interface. In this embodiment, the Channel containing alveolar epithelial cells may contain a gaseous medium simulating the fluid in an alveolar sac. In some embodiments, the upper channel may contain surfactants.

In another embodiment, an Airway-On-Chip (micro fluidic device) may comprise components such as: 1) bronchial epithelial cells (e.g. to model the bronchial tube epithelium 2) primary resident immune cells isolated from bronchial tube lamina propria, i.e. lamina propria-derived cells, 3) and vascular endothelial cells (e.g. HUVEC cells) to model the microvasculature of the bronchial airway. In one embodiment, the microfluidic device comprises top and bottom channels separated by a membrane, in this embodiment, the channel may contain a low level of medium for bathing the cells, with the remainder of the channel containing air for simulating a bronchial airway.

Figure 5:
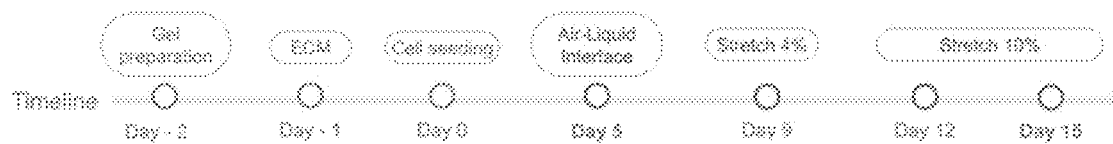
FIG. 5 Shows an exemplary schematic of one embodiment of an experimental timeline where Gel preparation is on Day-2; ECM is added to microchannels on Day 1; Cell seeding is on Day 0; Air-Liquid Interface is established by Day 5; Stretch of 4% begins on Day 9; Stretch of 10% begins on Day 12 which may continue up to Day 15.

A. Alveolus Lung On-Chips Evaluation of Epithelial Cells in the Upper Compartment In one embodiment, an exemplary timeline was used the preparing, seeding, and evaluating an Alveolus Lung-On-Chip, FIG. 5 shows an exemplary schematic of one embodiment of an experimental timeline where Gel preparation is on Day-2; ECM is added to microchannels on Day-1; Cell seeding is on Day 0; Air-Liquid Interface is established by Day 5; Stretch of 4% begins on Day 9; Stretch of 10% begins on Day 12 which may continue up to Day 15. Cell seeding included fibroblast cells within a gel, alveolar epithelial cells overlaying the gel in the upper channel, and endothelial cells in the lower channel. Incorporation of more physiologically relevant ECM (Elastin).

In some embodiments, mechanical stretch was provided using vacuum applied to vacuum channels for moving the membrane within the chip simulating in vivo breathing movements. In some embodiments, read-outs, i.e. evaluation, includes but is not limited to: on-chip immunostaining, e.g. staining to identify Type I and Type II pneumocytes; on-chip chemical staining, e.g. DAPI (4',6-Diamidino-2-Phenylindole, Dihydrochloride) for identifying nucleic acids, such as in cell nuclei; removal of tissue from the chip for microscopic evaluation after fixation, embedding, sectioning, and staining of tissues, e.g. H&E stain (i.e. Haemotoxylin and Eosin) comprising two dyes haematoxylin (blue/purple stain) for staining nuclei and eosin (pink stain) for staining acidophilic components in the tissue; mRNA expression in cells on-chip, including but not limited to RNAseq analysis, etc.

Thus, in one embodiment, an epithelial compartment on-chip was found to comprise Type I and Type II viable alveolar cells at 15 days post seeding. Further, epithelial cells on-chip formed an intact monolayer expressing cell-cell junction markers (E-cadberin, Connexin 43) and ion transporters (Na+ channels). A stromal compartment on-chip composed of viable fibroblasts embedded in 3D gel was discovered to remain stable over the entire course of the experiment, with the majority of fibroblasts staining positive for viable cell markers after 2 weeks in culture. H&E staining of tissues grown on-chip revealed preferential localization of fibroblasts beneath the epithelial layer. Moreover, microvascular lung endothelial cells on-chip formed a compact monolayer across the entire length of the vascular channel.

In fact, the inventors believe the ability to maintain primary human adult alveolar cells for 15 days, including up to 10 days under an ALI (i.e. air-liquid interface), in vitro, may be a novel finding. Furthermore, the co-cultivation of fibroblasts with alveolar epithelial cells promoted expression of epithelial markers such as Surfactant B and Aquaporin 5.

The following exemplary figures demonstrate, in part, these discoveries.

Figure 6A:
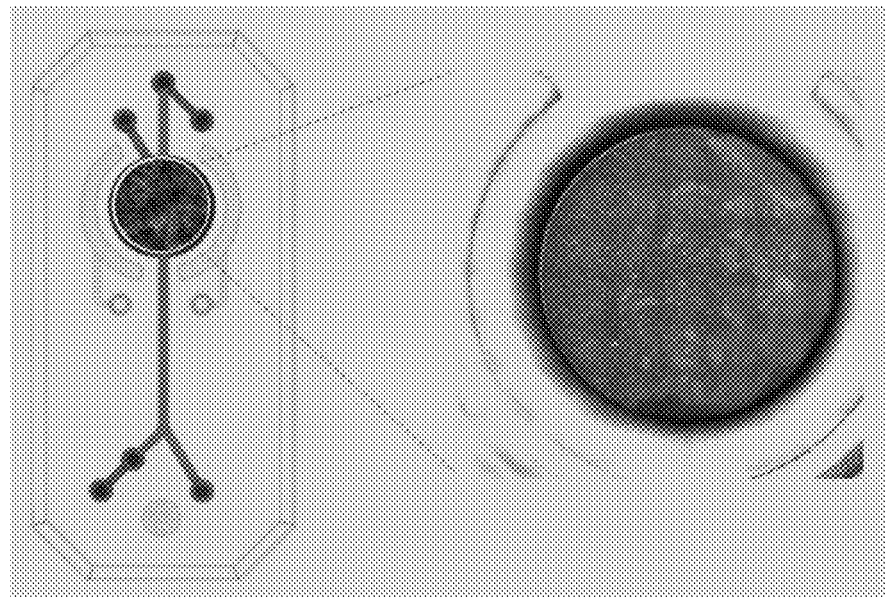
FIGS. 6A-B Show an exemplary schematic and micrographs of one embodiment of an epithelial surface: comprising alveolar epithelial cells forming a compact monolayer at 15 days post seeding.
Figure 6B:
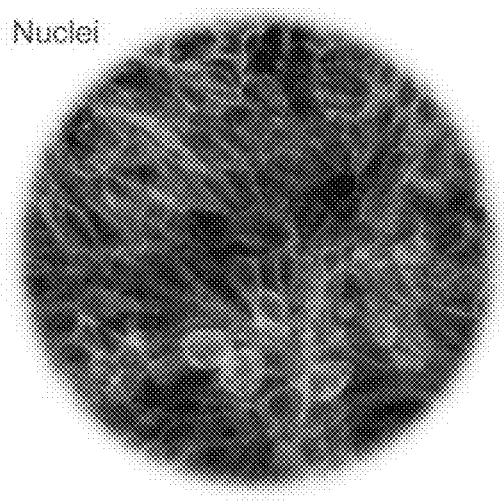

FIG. 6A-B shows an exemplary schematic and micrographs of one embodiment of an epithelial surface: comprising alveolar epithelial cells basting, a compact monolayer at 15 days post seeding. FIG. 6A shows an exemplary schematic of an open top chip with an exemplary micrograph of stained cells within the central chamber. FIG. 6B shows an enlarged view of the exemplary micrograph showing stained (red) Type I-Like pneumocytes co-stained for Actin (green); Nuclei (blue).

Figure 7:
FIG. 7 Shows an exemplary micrograph of an Epithelial layer growing on/within a gel layer in a Alveolus 3D gel system showing exemplary tissue architecture as a H&E stained alveolar cells. Thus, providing an epithelial surface in one embodiment of a 3D gel system on-chip further demonstrating the capability to support interaction of epithelial cells, endothelial cells, and fibroblast cells within a chip.

FIG. 7 Shows an exemplary micrograph of an Epithelial layer growing on/within a gel layer in a Alveolus 3D gel system showing exemplary tissue architecture as a H&E stained alveolar cells. Thus, providing an epithelial surface in one embodiment of a 3D gel system on-chip further demonstrating the capability to support interaction of epithelial cells, endothelial cells, and fibroblast cells within a chip.

A mixed population of Type I and Type II pneumocytes are present on-chip 2 weeks post seeding. FIG. 8A-B Shows exemplary micrographs demonstrating the detection of Type I and Type II Pneumocytes, HTI-56—a Type I (red); HTII-280 Type II (green) and DAPI stained—Nuclei (blue). FIG. 8A shows a co-stained area on-chip while the micrographs in FIG. 8B shows enlarged micrographs, using different filters, of the area outlined in white dotted line in FIG. 8A. Upper, micrograph showing both cell types in relation to nuclei; middle, micrograph showing Type I cells (red) in relation to nuclei; and lower, micrograph showing Type II cells (green) in relation to nuclei.

The presence of Type I-like and Type II pneumocytes were found using specific cellular markers. FIGS. 9A-B Show exemplary micrographs further demonstrating the presence of Type I-like and Type II pneumocytes on-chip using specific cellular markers, e.g. FIG. 9A pneumocyte Markers Mature Surfactant C Type II (green) and FIG. 9B Podoplanin Type I (red) in relation to nuclei (blue).

Alveolar epithelial cells display basolateral localization of E-Cadherin and Na/K-pump (Na+/K+ pump) at 15 days post seeding. FIGS. 10A-C Shows exemplary micrographs further demonstrating the presence of E-Cadherin and Na/K-pump proteins at 15 days post seeding. FIG. 10A An exemplary micrograph showing triple stained cells on-chip: Na+/K+ pump (red) E-Cadherin (green) Nuclei (blue), FIG. 10B An exemplary micrograph showing Na+/K+-pump (red). FIG. 10C An exemplary micrograph Showing E-Cadherin (green).

Figure 11:
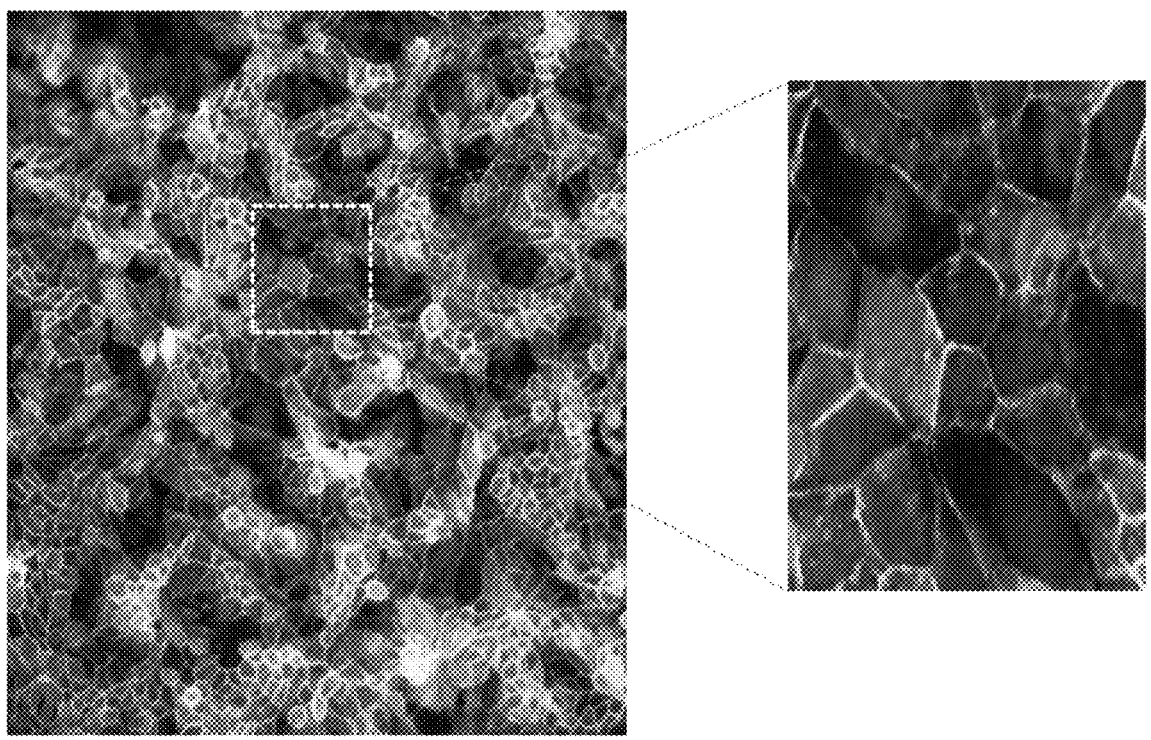
FIG. 11 Shows exemplary micrographs further demonstrating the presence of Epithelial Na+ channels (ENaC). E-Cadherin (green); EnaC (pink); and Nuclei (blue). Right micrograph is an enlargement of the area outlined in white dashes in the left micrograph. Connexin 43 is expressed on chip 15 days post seeding.

Epithelial cells express ENaC (scnn1) 15 days post seeding. FIG. 11 Shows exemplary micrographs further demonstrating the presence of Epithelial Na+ channels (ENaC), E-Cadherin (green); EnaC (pink); and Nuclei (blue). Right micrograph is an enlargement of the area outlined in white dashes in the left micrograph. Connexin 43 is expressed on-chip 15 days post seeding.

FIG. 12A-B Shows exemplary micrographs demonstrating the presence of Connexin 43—Gap Junction, Connexin 43 (grey); Nuclei (blue). FIG. 12A shows costained cells. FIG. 12A-B Shows Connexin 43 (grey) staining where yellow arrows point to individual cells.

B. Alveolus Lung On-Chip: Evaluation of Stromal Cells in the Stromal Compartment.

Human primary lung fibroblasts have been incorporated within the 3D stromal compartment of the chip, see highlighted area on-chip shown in FIG. 4C. Incorporation of Lung Fibroblasts On-Chip exemplary staining of rhodamine phalloidin, e.g. (PHDR1)Alexa Fluor® 488 Phalloidin, binds to F-actin proteins.

Figures 13A, 13B:
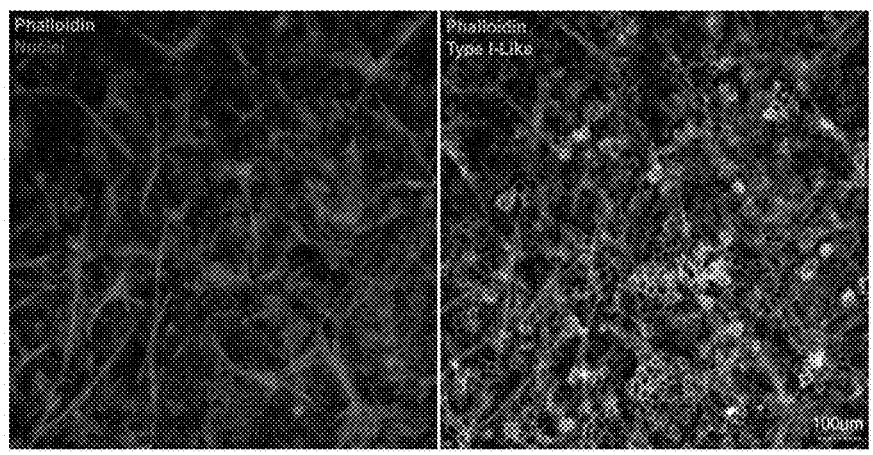
FIGS. 13A-B Show exemplary micrographs demonstrating the presence of lung fibroblasts.

FIGS. 13A-B Shows exemplary micrographs demonstrating the presence of lung fibroblasts. FIG. 13A lung fibroblasts stained for Phalloidin (pink) and Nuclei (blue). FIG. 13B Phalloidin (pink) and Type I-Like cells (green). White Bar=100 um.

FIGS. 14A-B Shows exemplary micrographs demonstrating assessment of Fibroblast Viability growing on-chip. FIG. 14A Maximum intensity projection of Z-Stack. FIG. 14B Live/Dead. FIG. 14C Phase Contrast (left) Phase Contrast Merge with Live/Dead. Live/dead staining shows high percentage of cell surviving on chip on day 15 post-seeding. Dead fibroblasts: rounded morphology and red nuclei. Live fibroblasts: typical elongated morphology and green cytoplasm.

FIGS. 15A-B Show exemplary micrographs demonstrating Distribution and Morphology of Alveolar Fibroblasts On-Chip. Fibroblasts are mostly localized underneath the epithelial surface, FIG. 15A, and display typical stellate shape, FIG. 15B.

Confocal Imaging at the Epithelial-Stromal Interface. FIGS. 16A-B Shows exemplary micrographs demonstrating Fibroblasts protrude towards the alveolar epithelium. FIG. 16A Type I (red) Type II (green) Fibroblasts (red) Nuclei (blue). FIG. 16B 3D animation.

Figure 20:
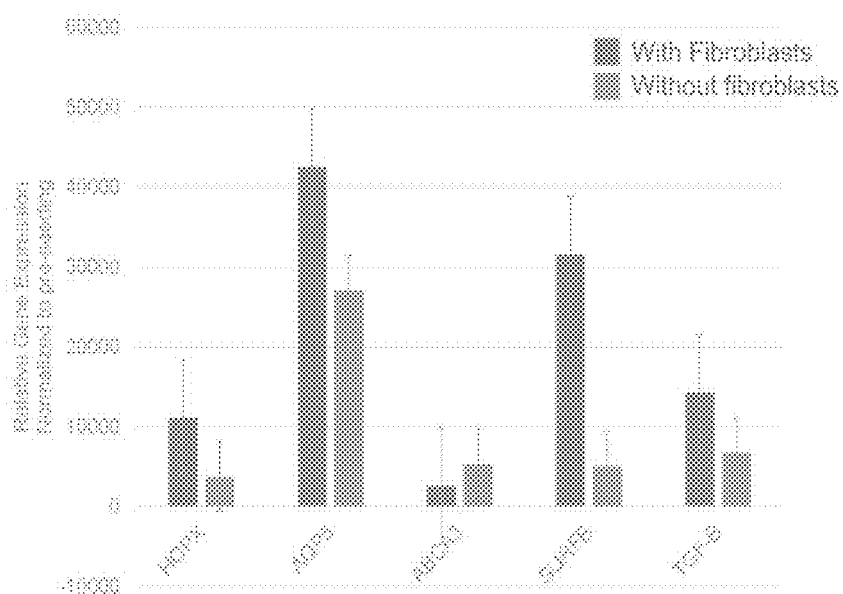
FIG. 20 Shows exemplary graph comparing gene expression of epithelial cells with and without fibroblast cells seeded into the stromal compartment. Gene expression at 15 days in culture.

Studies of the contribution of fibroblasts to epithelial cell maturation: Fibroblast-Epithelial Cell Interaction. FIG. 20 Shows exemplary graph comparing gene expression of epithelial cells with and without fibroblast cells seeded into the stromal compartment. Gene expression at 15 days in culture.

C. Alveolus Lung On-Chip: Evaluation of the Lower Vascular Compartment.

Figure 17:
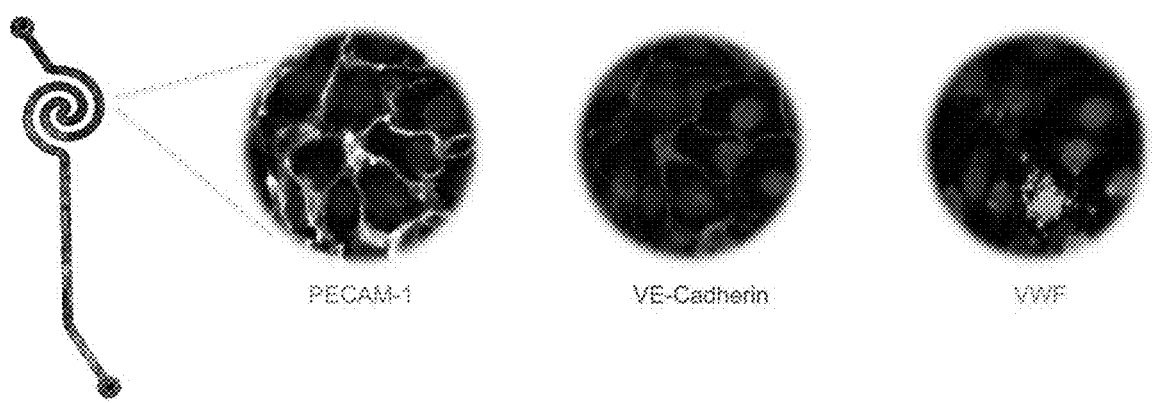
FIG. 17 Shows exemplary micrographs demonstrating microvascular endothelial cells expressing typical endothelial cells markers and covering the entire surface of vascular channel at 2 post seeding Left to right: PECAM-1: VE-Cadherin; and VWF.

FIG. 17 Shows exemplary micrographs demonstrating microvascular endothelial cells expressing typical endothelial cells markers and covering the entire surface of vascular channel at 2 post seeding. Left to right: PECAM-1; VE-Cadherin; and VWF.

D. Alveolus Lung On-Chip: Effect of Mechanical Force on the Alveolus Lung On-Chip.

In one embodiment of an alveolus Lung On-Chip, cells growing on-chip are exposed to both flow and stretching, as nonlimiting embodiments for growing under conditions of a mechanoactive environment. After growing under these conditions, i.e. alveolar cells grown for 15 days in mechanoactive environment (under constant flow and stretching) in Open-Top-Chips are positively stained with specific Type I and Type II antibodies (i.e. HTI/HTII). The stability of stromal compartment did not appear to be affected by stretch (as assessed at 15 days of stretch).

Mechanical strain promotes expression of Type II cell marker (HTII-Type II marker HT-II 280).

FIGS. 18A-E Show exemplary micrographs demonstrating effect of mechanical strain on epithelial cells while FIG. 18E shows a graph comparing the expression of these markers on cells, with and without strain. FIGS. 18A/B Without strain. FIGS. 18C/D with 10% Strain. Stained Type I cells are shown in red. Stained Type II cells are shown in green. FIG. 18E shows that strain increases expression of the HTII cell marker. Fluorescence Intensity per field view (a.u.) HTI vs. HTII.

Breathing motion (i.e. membrane under strain resulting in the movement of the cell layers) increases the number of Type II cells in the epithelia layer bringing the percentages closer to physiologically relevant proportions of Type II/Type I pneumocytes in vivo (40% vs. 60%, respectively).

FIG. 19A-B Shows exemplary graphs showing an exemplary effect of breathing motion on increasing expression of the Type II marker HT-II 280 vs. Type I markers.

FIG. 19A No strain resulting in 27% vs. 73%, respectively; and FIG. 9B Membrane under strain resulting in 44% vs. 56%, respectively.

E. Alveolus Lung On-Chip: Effect of ECM Composition on Epithelial Cells.

1. ECM: Effects on Gene Expression.

Gene expression data confirms that a combination of Collagen (CollI) IV, Fibronectin (FN) and Laminin (L) on-chip supports expression of both Type I (Aquaporin 5) and Type II pneumocytes (Surfactant B) better than any other combination tested, see FIGS. 21A-D and 22A-B.

TABLE 1

Genetic Markers for Epithelial (Pneumocyte) Cell Types.

| Gene | Marker for |
| --- | --- |
| Pdpn | Type 1 |
| HOPX | Type 1 |
| Aquaporin 5 | Type 1 |
| Pro-surfactant B | Type II |
| ABCA3 | Type II |
| Tgf-p | Epithelial to mesenchymal transition (EMT) |

FIGS. 21A-D Show exemplary effects of different ECM Composition on Epithelial Cells. FIG. 21A-C shows HTI-56 (Type I-Like cells) (red) and HTII-280 (Type II cells) (green) exposed to FIG. 21A Coll I; FIG. 21B Coll IV; FIG. 21C Coll IV-FN-L. FIG. 21D shows a graphical comparison markers demonstrating segregation of Type I-Like and Type II cell markers.

FIGS. 22A-B Show an exemplary gene expression of markers for FIG. 22A Type II Epithelial Cells and FIG. 22B Type I Epithelial Cells.

2. ECM: Effect of Elastin on Stromal Compartment.

As shown herein, a combination of Collagen IV, Fibronectin and Laminin promoted the expression and clear segregation of both Type I/Type II cell markers, see FIG. 21A-D.

Furthermore, a physiologically relevant concentration of elastin within the stromal compartment (20% Elastin-70% Bovine-collagen) was tested for its effects on cells growing on-chip. In fact, 70% (4/6 Chips tested) of the elastin-enriched gels were stable for 15 days on-chip. ALI was maintained for 10 days without compromising gel stability. Thus, cells growing on Collagen or Elastin-rich gel show comparable levels of viability. However, Elastin-rich gels appeared to promote more even (regular) cell morphology, see, FIGS. 23B-C.

FIGS. 23A-C FIG. 23A Shows an exemplary schematic timeline for use with a paraformaldehyde (PFA) fixed cell based readout. FIG. 23B Exemplary cell staining after growing on a Coll I Gel. FIG. 23C Exemplary cell staining after growing on a Coil I+Elastin (30%) Gel. Live cells (green), dead cells (debris) (red), nuclei (blue).

II. Chronic Inflammation of Lung And Airway Tissue.

Lung tissue comprises an epithelial layer and lamina propria with an overlying mucus-gel layer in the airway. Chronic inflammation of lung tissue involves alveoli epithelium, lamina propria, etc. as lung tissue, which can lead to irreversible scarring (pulmonary fibrosis). Examples of such diseases/disorders are provided below that may be modeled using microfluidic chips described herein.

A. Chronic Obstructive Pulmonary Disease (COPD).

Chronic obstructive pulmonary disease (COPD) refers to a group of inflammatory lung conditions. COPD in general refers to prolonged airflow obstruction and loss of the functional capacity of the lungs.

COPD affects at least 64 million people worldwide and is currently the 4th leading cause of death. COPD is a chronic disease, driven by recurrent cycles of inflammation that lead to tissue damage and remodeling with progressively worsening symptoms. There is no cure thus requiring lifelong health maintenance, for which current therapies merely reduce symptoms for variable time periods.

In some cases, COPD may arise from bacterial colonization of the lower respiratory tract. In one embodiment, biopsies or swabs are contemplated as sources of these cells for use with the microfluidic devices described herein.

Patients suffering from chronic bronchitis and emphysema that lead to breathing difficulties may develop other mucosal inflammatory diseases affecting the respiratory system. There are similarities in the pathological features of COPD, which may be the result of a common physiology of the respiratory systems within individual patients.

In one embodiment, the present invention contemplates a microfluidic model of inflammation of the lung comprising components such as alveolar cells (epithelium), alveolar lung macrophages (dust cells), dendritic cells, immune cells, endothelial cells, etc., in part for simulating a blood-air barrier.

B. Acute Respiratory Distress Syndrome (ARDS) and Infections.

The lung has an anatomically unique structure having a hierarchical branching network of conducting tubes that enable convective gas transport to and from the microscopic alveolar compartments where gas exchange occurs. The alveolus is the most important functional unit of the lung for normal respiration, and it is most clinically relevant in that it is the blood-gas barrier or interface, as well as the site where surfactants act to permit air entry and where immune cells, pathogens and fluids accumulate in patients with acute respiratory distress syndrome (ARDS) or infections, such as pneumonia.

In a non-limiting example embodiment, the device is configured to mimic operation of a lung, whereby lung epithelium cells self assemble on one surface of the ECM membrane and lung capillary endothelium cells self assemble on the opposite face of the same porous membrane. Lamina propria-derived cells can be placed on either or both surfaces. The device thereby allows simulation of the structure and function of a functional alveolar-capillary unit that can be exposed to both air-borne and blood-borne chemical, molecular, particulate and cellular stimuli to investigate the exchange of chemicals, molecules, and cells across this tissue-tissue interface through the pores of the membrane. The device impacts the development of in vitro lung models that mimic organ-level responses, which are able to be analyzed under physiological and pathological conditions. This system may be used in several applications including, but not limited to, drug screening, drug delivery, vaccine delivery, biodetection, toxicology, physiology and organ/tissue engineering applications. Additionally, the cells can be exposed to physiological mechanical strain (as described in U.S. Pat. No. 8,647,861, hereby incorporated by reference) to simulate breathing. In one embodiment, where the microfluidic device comprises top and bottom channels separated by a membrane, the membrane is stretched. Stretching mimics the mechanical forces experienced by a tissue-tissue interface, for example, in the lung alveolus during breathing, and thus provides the important regulation for cellular self-assembly into tissue structures and cell behavior. In one embodiment, the present invention contemplates long-term (weeks to months) cell culture and dynamic mechanical stretching of adjacent monolayers of lung epithelial or endothelial cells grown on the membrane at the same time.

In utilizing the membrane in simulating the tissue-tissue interface between the alveolar epithelium and pulmonary endothelium in the lung, one embodiment applies type I alveolar epithelial cells to the side of the membrane facing the first section (hereinafter top side of membrane) to mimic the epithelial layer. It is possible, however, to mix type I-like and type II-like alveolar epithelial cells at a ratio of approximately 7:13 to reconstruct the in vivo cellular composition of the alveolar epithelium. In the example method, lung microvascular endothelial cells are cultured on the opposite side of the membrane facing the second section (hereinafter bottom side of membrane). In the example method, negative pressure is cyclically applied to the device to cause the membrane to continuously expand and contract along its plane.

In one embodiment, the present invention contemplates in vitro models that simulate inflammatory responses of the lung at the organ level to allow study of how immune cells migrate from the blood, through the endothelium and into the alveolar compartment. One way this is achieved is by controlled and programmable microfluidic delivery of pro-inflammatory factors (e.g. IL-1.beta., TNF-.alpha., IL-8, silica micro- and nanoparticles, pathogens) as well as whole human blood flowing or medium containing circulating immune cells or direct contact with lamina propria-derived immune cells. Electrical resistance and short circuit current across the membrane may be monitored to study changes in the vascular permeability, extravasation of fluid and cell passage into the alveolar space during inflammatory responses. Fluorescence microscopy can be used to visualize dynamic cell motile behavior during the extravasation response.

It is not intended that the present invention be limited to any one particular use. It is contemplated that a variety of important areas of lung biology and physiology can be analyzed including but not limited to gas exchange, fluid/ion transport, inflammation, infection, edema/respiratory distress syndrome, cancer and metastasis development, drug delivery as well as drug screening, biodetection, and pulmonary mechanotransduction. In one embodiment, the system is contemplated for analysis of cell and tissue responses to drugs, chemicals, particulates, toxins, pathogens or other environmental stimuli for drug, toxin and vaccine screening, as well as toxicology and biodetection applications. The device may be used for studying complex tissue and organ physiology in vitro, as well as tissue and organ engineering in vivo with biocompatible or biodegradeable devices.

Thus, methods described here for use with Organ-On-Chips comprising lamina propria-derived cells can be extended to other mucosal tissues including the airway, lung and the skin. For example, a Lung-On-Chip (microfluidic device) may comprise components: 1) alveolar epithelial cells (e.g. to model the lung epithelium 2) primary resident immune cells isolated from alveolar lamina propria, i.e. lamina propria-derived cells, 3) and vascular endothelial cells (e.g. HUVEC cells) to model the microvasculature of the alveolar sac. In some embodiments, the upper channel may simulate a gas-liquid interface. In this embodiment, the channel containing alveolar epithelial cells may contain a gaseous medium simulating the fluid in an alveolar sac. In some embodiments, the upper channel may contain surfactants.

As another example, an Airway-On-Chip/Bronchial Tube-on-chip (microfluidic device) may comprise components: 1) bronchial epithelial cells (e.g. to model the bronchial tube epithelium 2) primary resident immune cells isolated from bronchial tube lamina propria, i.e. lamina propria-derived cells, 3) and vascular endothelial cells (e.g. HUVEC cells) to model the microvasculature of the bronchial airway. In this embodiment, the channel may contain a low level of medium for bathing the cells, with the remainder of the channel containing air for simulating a bronchial airway.

The present invention contemplates combining features from different embodiments. For a non-limiting example, lamina propria-derived cells from inflammatory tissue from the skin may be used in combination with bronchial epithelial cells. The present invention contemplates removing features from the above-indicated embodiments. For a non-limiting example, co-cultures of epithelial cells with endothelial cells and lamina propria-derived cells may have a feature removed. For example, subsets of cells isolated from lamina propria may be removed from the configuration in order to identify subsets of LP-derived cells contributing to specific disease phenotypes. The present invention contemplates adding features to the configuration in order to identify LP-cells initiating a specific disease phenotype, e.g. adding diseased LP-derived cells or immune cells isolated from diseased LP derived cells to microfluidic devices containing pre-disease or healthy cells. The present invention contemplates substituting features in the above-indicated embodiments. For a non-limiting example, ECM from commercial sources may be substituted with ECM isolated from humans.

III. Chronic Inflammation of Skin.

The present invention also contemplates a skin model in the form of a microfluidic device or layered structure. In one embodiment, the present invention contemplates a device or layered structure comprising i) fluidic channels covered by ii) a porous membrane, said membrane comprising iii) lamina propria derived cells and said membrane positioned below iv) a gel matrix comprising fibroblasts and keratinocytes. In one embodiment, the gel matrix (and or cells) is covered by a removable cover. In one embodiment, the fibroblasts are within the gel matrix and the keratinocytes are on top of the gel matrix. In one embodiment, the keratinocytes comprise more than one layer on top of the gel matrix.

In one embodiment, the present invention contemplates a construct comprising a "dermis" with fibroblasts embedded in a matrix having a thickness between 0.2 and 6.0 mm, e.g. a collagen I gel matrix, and an "epidermis", which is comprised of keratinocytes, e.g. stratified, differentiated keratinocytes. A matrix such as a collagen gel provides scaffolding, nutrient delivery, and potential for cell-to-cell interaction. In one embodiment, the construct further comprises functional lamina propria-derived cells.

It is not intended that the present invention be limited to the thickness of the gel matrix. However, a preferred range of thickness is between 0.2 and 6 mm, and more preferably between 0.5 mm and 3.5 mm, and still more preferably approximately 1-2 mm. In a preferred embodiment, the gel matrix is stretchable. In a preferred embodiment, the gel matrix is stretched in a manner such that the entire gel matrix expands, not just a portion of the gel matrix (such as only the bottom or top of the matrix). In a preferred embodiment, the gel matrix is stretched by vacuum channels that are designed to provide pneumatic stretching that is uniform across the thickness of the gel.

It is not intended that the skin model be limited to just one type of keratinocyte. Indeed, the model can be used with many types of cells of the integumentary system including but not limited to Keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, and Hair matrix cells (stem cell). In one embodiment, human foreskin keratinocytes are employed.

IV. Blood Brain Barrier (BBB) and Microglial Cells.

Brain microvascular endothelial cells (BMEC) are interconnected by specific junctional proteins forming a highly regulated barrier separating blood and the central nervous system (CNS), the so-called blood-brain-barrier (BBB). Together with other cell-types such as astrocytes or pericytes, they form the neurovascular unit (NVU), which specifically regulates the interchange of fluids, molecules and cells between the peripheral blood and the CNS.

The blood-brain barrier is of major clinical relevance because dysfunction of the blood-brain barrier leads to degeneration of the neurovascular unit, and also because drugs that are supposed to treat neurological disorders often fail to permeate the blood-brain barrier. Due to its importance in disease and medical treatment, it would be highly advantageous to have a predictive model of the human blood-brain barrier that recapitulates aspects of the cerebral endothelial microenvironment in a controlled way.

In some embodiments, microfluidic platforms or "chips" for testing and understanding the blood brain barrier are provided, and, more specifically, for understanding the factors that contribute to microglial (specialized macrophage) function and immunological responses in the brain.

In one embodiment, the present invention contemplates a layered structure comprising i) fluidic channels covered by ii) a porous membrane, said membrane comprising iii) a layer of brain microvascular endothelial cells and said membrane positioned below iv) a gel matrix (or other porous volume). The present invention contemplates, in one embodiment, living neuronal cells (e.g. neurons, astrocytes, pericytes, etc.) on, in or under the gel matrix. In one embodiment, the layered structure further comprises microglial cells It is preferred that some portion of the device can be opened for access to these cells. In one embodiment, the device comprises a removable top. The gel can be patterned to control the positioning and/or orientation of the cells or portions thereof. For example, the pattern on the gel matrix can direct neurite growth for neurons seeded on the patterned surface.

Microglia are the primary immune cells of the CNS, and are highly similar to peripheral macrophages. They act as the major inflammatory cell type in the brain, and respond to pathogens and injury by becoming "activated"—a process whereby they rapidly change morphology, proliferate and migrate to the site of infection/injury where they phagocytose and destroy pathogens as well as remove damaged cells. As part of their response they secrete cytokines and chemokines, as well as prostaglandins, NO and reactive oxygen species, which help to elevate and direct the immune response. Additionally, they are instrumental in the resolution of the inflammatory response, through the production of anti-inflammatory cytokines such as Il-10. While seeking out and destroying pathogens is an important and protective role, microglia have also been extensively studied for their harmful roles in neurodegenerative diseases and brain injuries, such as Alzheimer's disease, Parkinson's disease, ischemic injury, and traumatic brain injuries.

IV. Cancer.

In some embodiments, microfluidic platforms or "chips" for testing and understanding cancer are provided, and, more specifically, for understanding the factors that contribute to cancer invading tissues and causing metastases. Tumor cells are grown on microfluidic devices with other non-cancerous tissues, including but not limited to, lamina propria-derived cells, stromal cells, epithelial cells, cells of the immune system, etc., under conditions that simulate tumor invasion. The interaction with immune cells can be tested to inhibit this activity.

Therefore, the present invention contemplates, in one embodiment, a method comprising: 1) providing a) living tumor cells and b) a microfluidic device comprising a body having a microchannel (optionally located centrally) therein; and an at least partially porous membrane positioned within the microchannel and along a plane, the membrane configured to separate the microchannel to form a first microchannel and a second microchannel, the membrane comprising a top surface and a bottom surface, said i) top surface comprising living lamina propria-derived cells; and 2) introducing said living tumor cells into said microfluidic device under conditions such that at least a portion of said living tumor cells contact with said lamina propria-derived cells.

Tumor cells are contemplated to be placed in microfluidic devices or chips. As used herein, malignant neoplasia are referred to as "cancer" and characterized by tumor cells that typically will ultimately metastasize into distinct organs or tissues. Malignant neoplasia includes solid and hematological tumors. "Solid tumors" are exemplified by tumors of the breast, bladder, bone, brain, central and peripheral nervous system, cervix, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, sarcoma, skin (e.g. melanoma), small intestine, stomach (or gastric cancer), soft tissue, testis, ureter, vagina and vulva. Malignant neoplasias include but are not limited to: inherited cancers exemplified by Retinoblastoma and Wilms tumor and a number of tumors included in Li Fraumeni syndrome, e.g. hereditary colon cancer. In addition, malignant neoplasia includes primary tumors in said organs and corresponding secondary tumors in distant organs ("tumor metastases") as well as circulating tumor cells. Hematological tumors are exemplified by aggressive and indolent forms of leukemia and lymphoma, namely non-Hodgkins disease, chronic and acute myeloid leukemia (CMLiAML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies (e.g. Kaposi's sarcoma).

Agents are contemplated for testing on the cancer chip. A variety of classes of agents are contemplated, including but are not limited to (i) kinase inhibitors such as e.g. Glivec, ZD-1839/Iressa, Bay43-9006, SUI1248 or OSI-774/Tarceva; (ii) proteasome inhibitors such as PS-341; (iii) histone deacetylase inhibitors like SAHA, PXD101, MS275, MGCD0103, DepsipeptideiFK228, NVP-LBH589, Valproic acid (VPA) and butyrates; (iv) heat shock protein inhibitors like 17-allylaminogeldanamycin (17-MG); (v) vascular targeting agents (VAT) and anti-angiogenic drugs like the VEGF antibody Avastin or the KDR tyrosine kinase inhibitor PTK787/ZK222584; (vi) monoclonal antibodies such as Herceptin or MabThera/Rituxan or C225/Erbitux as well as mutants and conjugates of monoclonal antibodies and antibody fragments; (vii) oligonucleotide based therapeutics like G-3139/Genasense; (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors. In one embodiment, the PHSCN peptide is contemplated, in the form of Ac—PHSCN—$NH_2$ where all the amino acids are L-isomers or where one or more amino acids are D-isomers as described in U.S. Pat. No. 8,940,701, hereby incorporated by reference.

DETAILED DESCRIPTION OF THE INVENTION

Organ-On-Chip with Lamina Propria-Derved Cells.

As described and shown herein, chips containing co-cultures of epithelial cells (e.g. skin cells) and vascular endothelial cells (e.g. HUVECs) in the presence of lamina propria (LP) derived cells (LPDCs) are provided, as examples of Organ-on-chips.

These Organ-on-chip cultures with LPDCs are contemplated to show physiological and morphological changes in epithelial cell layers directly related to the source of LP derived cells. In particular, resident immune cells, i.e. lamina propria-derived cells (including but not limited to resident immune cells, such as B cells, T cells, dendritic cells, monocytes, macrophages, and innate lymphoid cells) may be isolated from healthy people and patients (including inflamed and non-inflamed regions of patient tissue) for use in this chip based co-culture system. Specifically, methods of use include but are not limited to comparing cultures containing LPDC cultures from different sources and/or different sites of the body; comparing epidermal cell cultures from different sources and/or different sites of the body; comparing cultures for individual or combinations of agent/drug/compound(s) for determining effects of such agent; comparing pathogen/microbiome effects; comparing cytokine expression; comparing challenges (additions) of certain cytokines/chemokines, individually or in combinations; etc.

Thus additional features related to embodiments of the present inventions to providing co-cultures of epithelial cells, vascular endothelial cells and resident immune cells (i.e. lamina propria-derived cells) include but are not limited to providing a capability for measuring amounts of secreted cytokines; epithelial cell barrier function measurements; determining effects of bacterial antigens, such as in a loss-of-barrier-function bioassay, including with bacterial antigen treatments; etc.

Accordingly, some embodiments described herein relate to devices for simulating a function of epithelial tissue (also referred to as "organ-on-a-chip device"). The organ-on-a-chip microfluidic devices described herein can be used to simulate at least one or more (e.g., 1, 2, 3, 4, 5 or more) phenotypes and/or functions of a variety of tissues.

In one embodiment, the present invention contemplates incorporating lamina propria-derived cells (such as resident immune cells, e.g. leukocytes, (i.e. white blood cells), mononuclear cells, resident fibroblasts, etc.) in the chip embodiments described herein. Thus, in one embodiment, LPDCs are incorporated into an embodiment of the organ-on-chip. This can be done in a variety of combinations. In one embodiment, the LPDCs are deposited underneath epithelial cells and on top of an extracellular matrix (ECM) composition coated membrane (e.g. with a gel overlay or simply underneath the epithelial cells, i.e. without a gel overlay). In one embodiment, the LPDCs are further overlaid with a layer of ECM, i.e. ECM overlay, before depositing the epithelial layer. In one embodiment, however, the LPDCs are overlaid with an actual gel. In one embodiment, the LPDCs are deposited within a gel layer. The same or similar approaches can be used to incorporate other tissue-specific or resident cells (whether immune cells, fibroblasts, mixtures, etc.).

The lamina propria-derived cells can be used for different degrees of purification or cell isolation: used wholesale, used with the cells isolated from ECM components, and isolated for specific cell types. Thus, in one embodiment, a full milieu of cell types was isolated and used in microfluidic devices described herein. An example of a full milieu of cell types used as a lamina propria-derived cell population, include but are not limited to stromal cells, fibroblasts, and resident immune cells. Examples of stromal cells include but are not limited to connective tissue cells, e.g. fibroblasts, myofibroblasts, etc., located in the mucosa, submucosa, etc. In fact, cells comprising LP-derived cells may not be limited to the mucosa. In some embodiments, Examples of resident immune cells including but are not limited to innate immune cells such as natural killer cells, γδ+ T cell receptor cells, adaptive immune cells, such as mononuclear cells, including monocytes, macrophages, basal cells, eosinophils, plasma cells, T cells, such as CD8+CD4+, double positive, and dendritic cells, immature through mature, are found here. As another example, purified/isolated LP-derived cell populations were used in microfluidic devices described herein. In some embodiments LP-derived cells may be used directly after isolation. In some embodiments, LP-derived cells are expanded in cultures before adding to a microfluidic chip of the present inventions.

Thus, in other embodiments, other types of purifications or isolations are possible, including cells extracted from or isolated from lamina propria (as lamina propria derived cells, or LPDCs). In a preferred embodiment, resident immune cells are extracted and purified. In one embodiment, lymphoid follicles are not included. In one embodiment, lymphoid follicles are included. Such that the presence of a lymphoid follicle in tissue used for isolation or extraction of cells may be determined by observation of the lamia propria tissue by optical microscopy prior to removal of cells. In one embodiment, capillary endothelial cells are extracted and purified.

In one embodiment stromal tissue is used for isolation of stromal cells, LP derived cells, etc.

Other embodiments contemplated for mimicking disease is by manipulating differentiation and/or activation stages of T cells. Thus, in yet another embodiment, pre-differentiated T-cells are added to a chip of the present inventions. In one embodiment, the present invention contemplates the use of published protocols to differentiate naïve T-cells from peripheral blood mononuclear cells (PBMCs) isolated from blood samples towards a T-helper cell fate. With this approach, T-helper profiles can be generated that mimic different types of autoimmune diseases, including diseases described herein.

Cytokine Expression in Organ-On-Chips Cytokine expression is contemplated for assaying using Organ-On-Chips. In the organ-on-chip, the presence of LPDC is contemplated to effects cytokine response and inflammation. Cytokines are contemplated for testing include but are not limited to TGF-beta, interleukin-2, interleukin-4, interleukin-12, interleukin-17, interleukin-21, interleukin-22, interleukin-23, interleukin-27, TNF-alpha, and Interferon-gamma.

Exemplary Organ-On-A-Chip Devices and Methods.

Figure 1B:
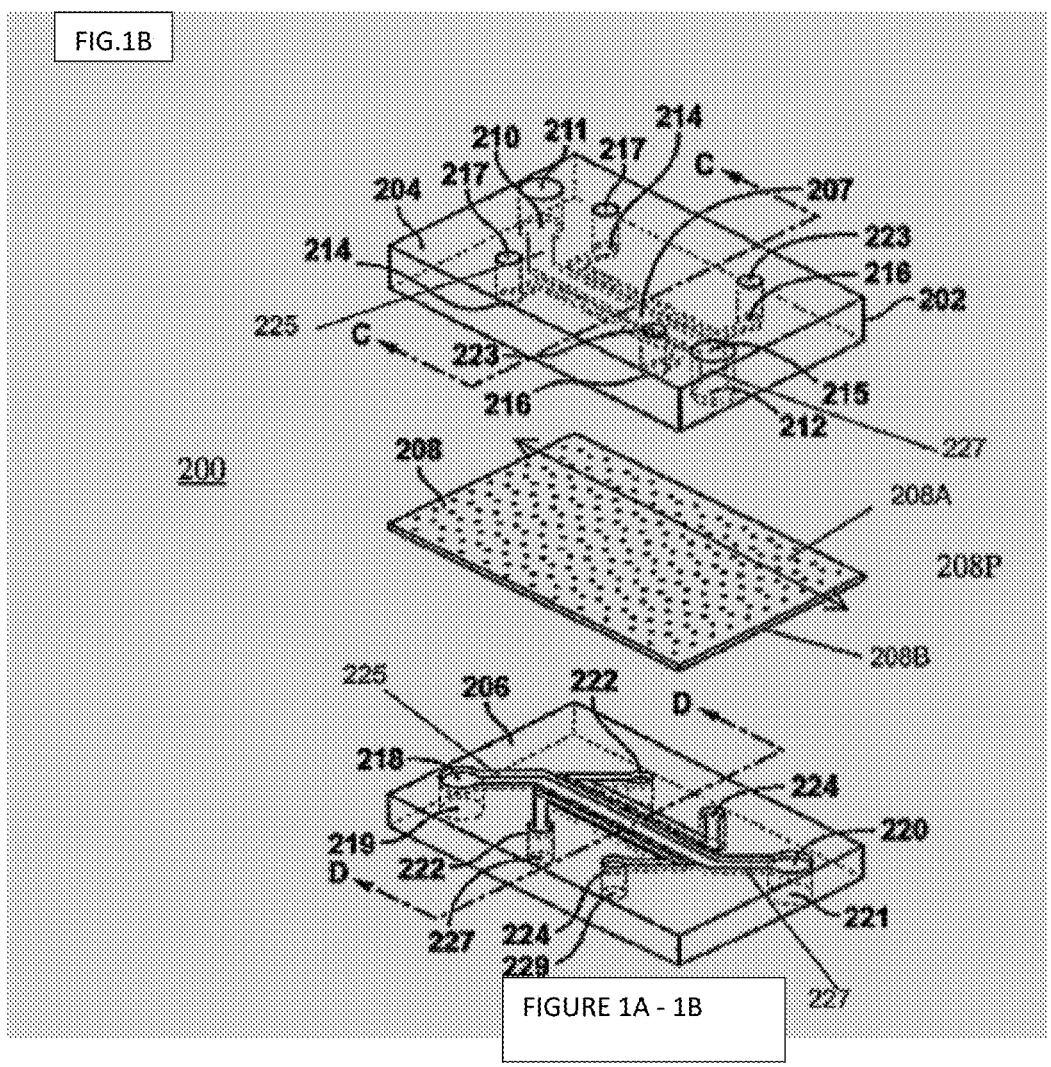
FIG. 1B illustrates an exploded view of the device in accordance with an embodiment, showing a microfluidic channel in a top piece and a microfluidic channel in a bottom piece, separated by a membrane.

FIG. 1A-1B illustrates a perspective view of one embodiment of a microfluidic device in accordance with some embodiments described herein. For example, as shown in FIGS. 1A-1B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is merely exemplary and not limited to the configuration shown in FIGS. 1A-1B. While operating channels 252 (e.g., as a pneumatics means to actuate the membrane 208, see below for information on membrane 208 and see the International Appl. No. PCT/US2009/050830 for further details of the operating channels, the content of which is incorporated herein by reference in its entirety) are shown in FIGS. 1A-1B, they are not required in all of the embodiments described herein. In some embodiments, the devices do not comprise operating channels on either side of the microchannel. In other embodiments, the devices described herein can be configured to provide other means to actuate the membrane, e.g., as described in the International Pat. Appl. No. PCT/US2014/071570, the content of which is incorporated herein by reference in its entirety.

In some embodiments, various organ chip devices described in the International Patent Application Nos. PCT/US2009/050830; PCT/US2012/026934; PCT/US2012/068725; PCT/US20121068766; PCT/US2014/07161; and PCT/US2014/071570, the contents of each of which are incorporated herein by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof.

As used herein, the term "rigid" refers to a material that is stiff and does not bend easily, or maintains very close to its original form after pressure has been applied to it.

The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure.

In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof.

As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally or alternatively, at least a portion of the first structure 204 and/or second structure 206 can be made of non-flexible or rigid materials like glass, silicon, hard plastic, metal, or any combinations thereof.

The device in FIG. 1A can comprise a plurality of access ports 205. In addition, the branched configuration 203 can comprise a tissue-tissue interface simulation region or regions (such as a region on the membrane 208 in FIG. 1B) where cell behavior and/or passage of gases, chemicals, molecules, particulates and cells are monitored. FIG. 1B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204 and 206 when the portions 204 and 206 are mounted onto one another to form the overall body.

The microchannel(s) in the microfluidic devices can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 1B illustrates an exploded view of the device in accordance with an embodiment. As shown in FIG. 1B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 1B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

A Membrane Located in Between the First Structure and Second Structure.

In one embodiment, the membrane 208 is oriented along a plane between the first chamber 204 and the second chamber 206. It should be noted that although one membrane 208 is shown, more than one membrane 208 can be configured in devices which comprise more than two chambers.

The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass through. In some embodiments, a selectively-permeable membrane can allow certain cell types to pass through but not other cell types.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell-binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In some embodiments, cells are cultured on and/or under the membrane under flow conditions. In some embodiments, there is a steady-state perfusion of the cells. In other embodiments described herein, the devices can comprise a flowing culture medium in the first chamber and/or the second chamber, wherein the flowing culture medium generates a shear stress. Based on the viscosity of the culture medium and/or dimensions of the chambers, one of skill in the art can determine appropriate flow rates of culture medium through the chambers to achieve desired shear stress. In some embodiments, the flow rate of the culture medium through the first chamber can range from about 5 μL/hr to about 50 μL/hr. In some embodiments, the flow rate of the culture medium through the second chamber can range from about 15 μL/hr to about 150 μL/hr. Thus, in one embodiment, fluidic shear forces are generated.

Optional Vacuum Channels

Fluidic channels in devices of the present inventions are optionally flanked by two vacuum channels that allow the pneumatically actuated stretching forces mimicking peristalsis, for a non-limiting example, bronchial spasms. In some embodiments, stretching forces are for stretching an epithelial layer. In one embodiment, mechanical forces are generated.

The Use of a Cartridge with Said Device.

In some embodiments, the devices described herein can be placed in or secured to a cartridge. In accordance with some embodiments described herein, the device can be integrated into a cartridge and form a monolithic part. Some examples of a cartridge, such as a cartridge assembly for transporting fluid into or out of one or more fluidic devices, are described in the International Patent App. No. PCT/US2014/047694 (published as WO 2015013332: Microfluidic Cartridge Assembly), the content of which is incorporated herein by reference in its entirety. The cartridge can be placed into and removed from a cartridge holder that can establish fluidic connections upon or after placement and optionally seal the fluidic connections upon removal. In some embodiments, the cartridge can be incorporated or integrated with at least one sensor, which can be placed in direct or indirect contact with a fluid flowing through a specific portion of the cartridge during operation.

Exemplary Devices for Simulating a Function of a Tissue.

Some embodiments described herein relate to devices for simulating a function of a tissue, in particular an epithelial tissue. In one embodiment, the device generally comprises (i) a first structure defining a first chamber; (ii) a second structure defining a second chamber, and (iii) a membrane located at an interface region between the first chamber and the second chamber to separate the first chamber from the second chamber, the membrane including a first side facing toward the first chamber and a second side facing toward the second chamber. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Ecm Coating.

To determine optimum conditions for cell attachment, the surface-treated material (e.g., APTES-treated or plasma-treated PDMS) can be coated with an ECM coating of different extracellular matrix molecules at varying concentrations (based on the resulting cell morphology and attachment).

Ecm Overlay.

The ECM overlay is typically a "molecular coating," meaning that it is done at a concentration that does not create a bulk gel. In some embodiments, an ECM overlay is used. In some embodiments, an ECM overlay is left in place throughout the co-culturing. In some embodiments, an ECM overlay is removed, e.g. when before seeding additional cells into a microfluidic device. In some embodiments, the ECM layer is provided by the cells seeded into the microfluidic device.

Although cells described for use in an organ-on-chip make their own ECM, it is contemplated that ECM in predisease and diseased states may contribute to inflammatory states. Further, the protein microenvironment provided by ECM also affects cells. Thus it is contemplated that tissue-derived ECM may carry over a disease state. Therefore, in addition to the ECM described herein, ECM used in microfluidic devises of the present inventions may be tissue-derived (native) ECM. In one embodiment, a device comprising tissue-derived ECM may be used as described herein, to identity contributions to healthy or disease states affected by native ECM. For example, ECM may be isolated from biopsies of healthy, non-disease and disease areas as tissue-derived ECM. Isolates for use may include cells within or attached or further processed to remove embedded cells for use in the absence of the cells. Additional examples of ECM materials include but are not limited to Matrigel®, Cultrex®, ECM harvested from humans, etc.

Matrigel® is a trade name for a solubilized basement membrane preparation extracted from the Engelbreth-Holm-Swarm (EHS) mouse sarcoma, a tumor rich in such ECM proteins as laminin (a major component), collagen IV, heparin sulfate proteoglycans, entactin/nidogen, and a number of growth factors as produced and marketed by Corning Life Sciences. Matrigel® gels to form a reconstituted basement membrane. Versions of Matrigel® include BD Matrigel® (Basement Membrane) Matrix, offered as Standard, Growth Factor Reduced, Growth Factor Reduced-High Concentration (HC) and Growth Factor Reduced-Phenol Red-Free formulations, BD Matrigel® hESC-qualified Matrix, by BD Biosciences.

Trevigen, Inc. markets other ECM versions of BME harvested as a soluble form of basement membrane purified from Engelbreth-Holm-Swarm (EHS) tumor cells under the trade name Cultrex® Basement Membrane Extract (BME). Cultrex® extract gels at 37° C. to form a reconstituted basement membrane. The major components of Cultrex® BME include laminin, collagen IV, entactin, and heparin sulfate proteoglycan. Several forms Cultrex® are offered by Trevigen as: Cultrex® Reduced Growth Factor Basement Membrane Extract, Type R1. Type R1 matrix provides a proprietary formulation that has higher tensile strength when compared to other Cultrex® products, i.e. Cultrex® BME, Cultrex® BME Type 2 and Cultrex® BME Type 3. Type R1 has a higher concentration of entactin, one of the BME components that connect laminins and collagens reinforcing the hydrogel structure. Cultrex® BME Type R1 has been specifically designed to culture tissue organoids. BME type R1 supports culture of organoids. In a Tube formation assay ~BME type R1 promotes formation of capillary-like structures by human (HBMVEC; HUVEC). Under a Cultrex® Organoid Qualified BME, Type 2 designation, several formulations of Cultrex® BME are described for organiod culture, Cultrex® Reduced Growth Factor Basement Membrane Extract. Additional products that might find use include but are not limited to Cultrex® 3-D Culture Matrix® Reduced Growth Factor Basement Membrane Extract, Cultrex® Basement Membrane Extract, Type 3, PathClear®. The PathClear® designation means that in addition to standard sterility, endotoxin and MAP testing, the basement membrane extract is tested by PCR and is clear of 31 pathogens and viruses, including lactate dehydrogenase elevating virus (LDEV). Cultrex® BME Type 2 provides a formulation with a higher in tensile strength when compared to the original BME, while Cultrex® BME Type 3 is physiologically aligned with the in vivo solid tumors environment.

II. Closed Top Chips.

The present disclosure relates to organ-on-chips, such as fluidic devices comprising one or more cells types for the simulation one or more of the function of epithelial components. Accordingly, the present disclosure additionally describes closed-top organ-on-chips, see, e.g. schematics in FIG. 1A-C.

Figure 1C:
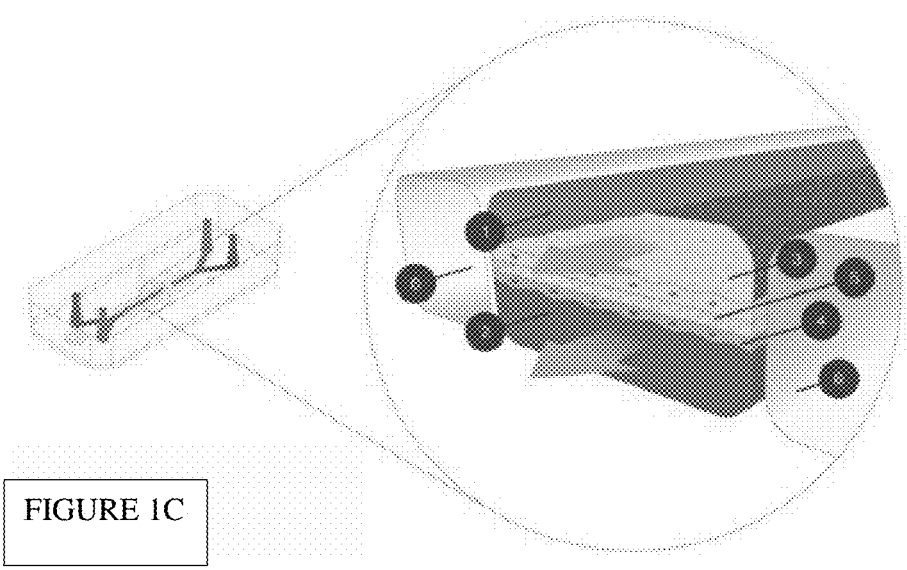
FIG. 1C Shows cells in relation to device parts, e.g. upper and lower channels and optional vacuum chamber. 1. Air channel; 2. Vascular channel (lower); 3. Lung tissue (e.g. epithelial cells); 4. Capillaries e, g, endothelial cells); 5. Membrane; and 6. Vacuum Channels.

An exemplary schematic of one embodiment of a closed top chip is shown in FIG. 1C. FIG. 1C shows cells in relation to device parts, e.g. upper and lower channels and optional vacuum chamber. 1. Air channel; 2. Vascular channel (lower); 3. Lung tissue (e.g. epithelial cells); 4. Capillaries (e.g. endothelial cells); 5. Membrane; and 6. Vacuum Channels.

A. Closed Top Microfluidic Chips without Gels.

In one embodiment, closed top organ-on-chips do not contain gels, either as a bulk gel or a gel layer. Thus, in one embodiment, the device generally comprises (i) a first structure defining a first chamber; (ii) a second structure defining a second chamber, and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips with Gels.

In one embodiment, closed top organ-on-chips do contain gels, such as a gel layer, including but not limited to a gel matrix, hydrogel, bulk gels, etc. Thus, in one embodiment, the device generally comprises (i) a first structure defining a first chamber, (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips with Simulated Lumens.

A closed top organ-on-chip comprising a gel-lined simulated lumen may be used for generating a more physiological relevant model of epithelial tissue. In some embodiments, closed top organ-on-chips further comprise a gel simulated three-dimensional (3-D) lumen. In other words, a 3-D lumen may be formed using gels (e.g. viscous fingers) and/or mimicking tissue folds. In a preferred embodiment, the gel forms a lumen, i.e. by viscous fingering patterning.

Using viscous fingering techniques, e.g. viscous fingering patterning, a simulated lumen may be formed. As one example, viscous fingers may be formed and used to mimic epithelial projections in the respiratory system.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning." J Lab Autom. 2012 April; 17(2): 96-103. Author manuscript; available in PMC 2012 Jul. 16, herein incorporated by reference in its entirety. In one example of a viscous finger patterning method for use with microfluidic organ-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium.

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated lumens.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular miroenvironment, (e.g. MATRIGEL®. In some embodiments, the first and second permeable matrixes can each independently comprise a polymer matrix. Methods to create a permeable polymer matrix are known in the art, including, e.g. but not limited to, particle leaching from suspensions in a polymer solution, solvent evaporation from a polymer solution, sold-liquid phase separation, liquid—liquid phase separation, etching of specific "block domains" in block co-polymers, phase separation to block-co-polymers, chemically cross-linked polymer networks with defined permeabilities, and a combination of two or more thereof.

Another example for making branched structures using fluids with differing viscosities is described in "Method And System For Integrating Branched Structures In Materials" to Katrycz, Publication number US20160243738, herein incorporated by reference in its entirety.

Regardless of the type of lumen formed by a gel and/or structure, cells can be attached to theses structures either to lumen side of the gel and/or within the gel and/or on the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, LPDCs may be added within the gel, or below the gel, on the opposite side of the lumen. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Microfluidic Chips.

Figure 2:
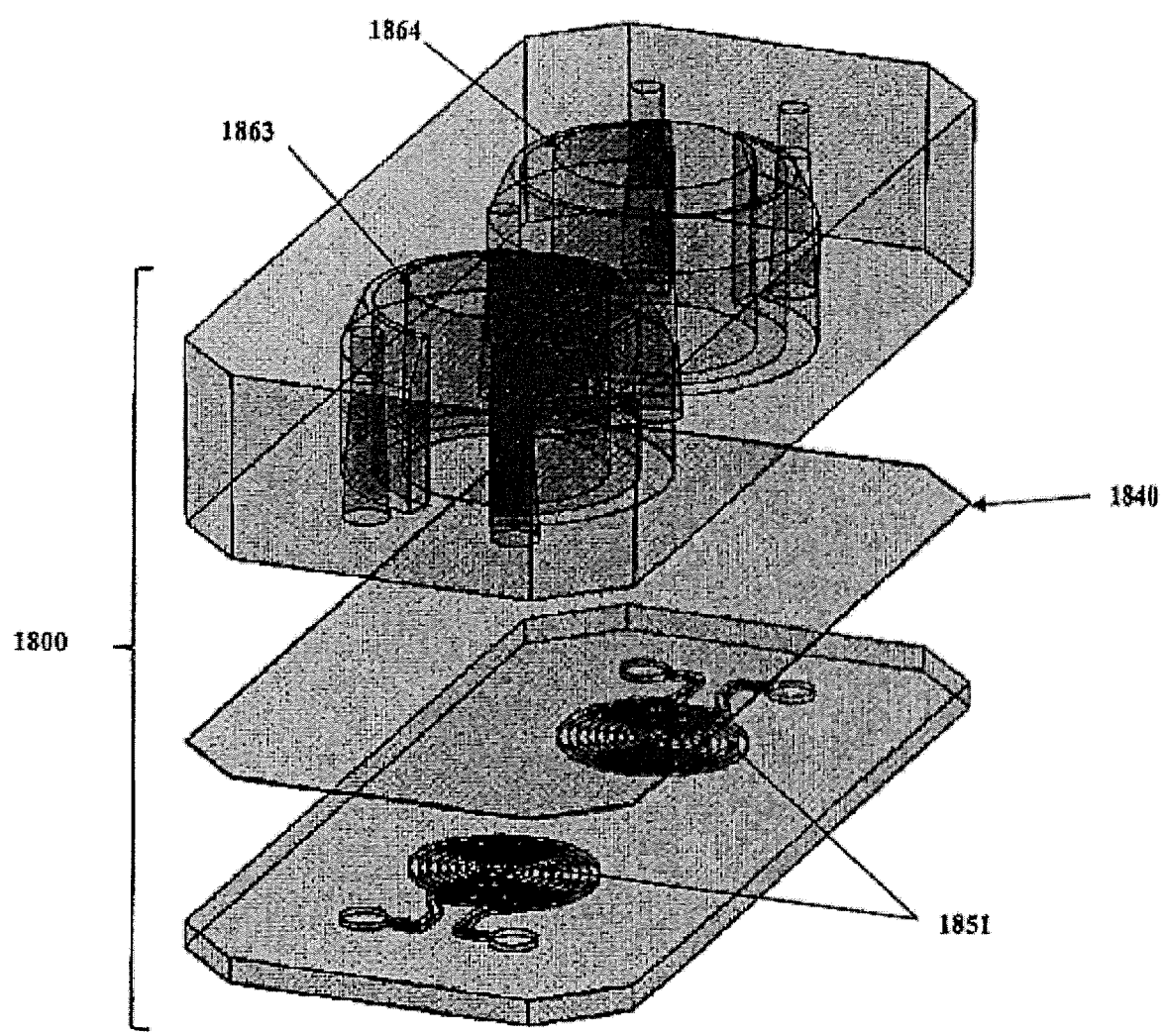
FIG. 2 Shows an exemplary schematic of an open top microfluidic chip.

The present disclosure relates to organ-on-chips, such as fluidic devices comprising one or more cells types for the simulation one or more of the function of organ components. Accordingly, the present disclosure additionally describes open-top organ-on-chips, see, e.g. schematic in FIG. 2. FIG. 2 shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated organ tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover, and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein, including but not limited to Eye-On-Chip, etc.

Figure 3:
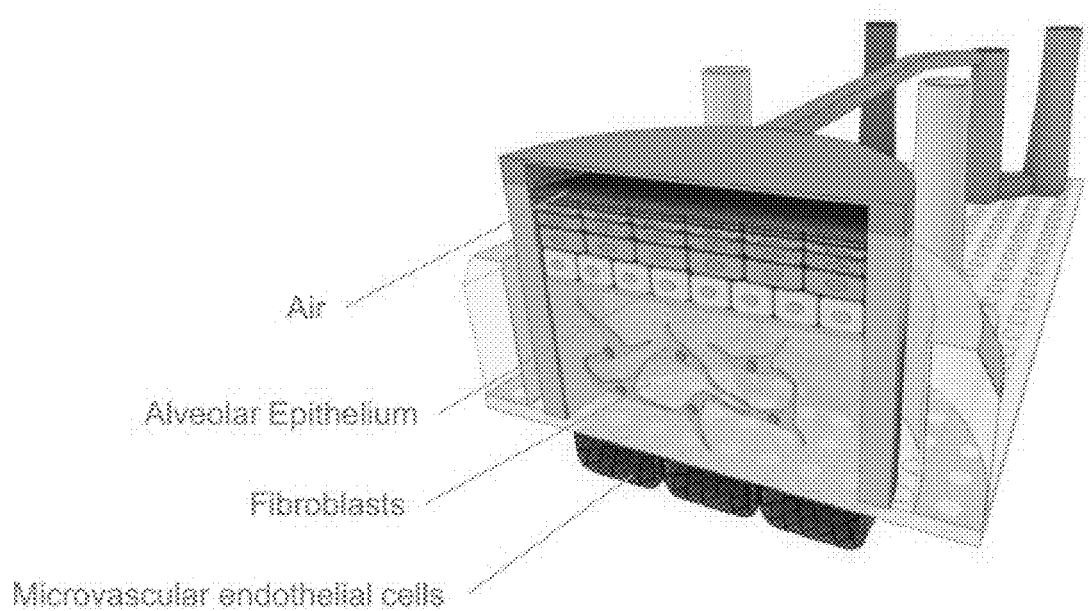
FIG. 3 Shows an exemplary schematic of one embodiment of a 3D Alveolus Lung Ort-Chip demonstrating an air layer on top of an alveolar epithelium layer overlaying a stromal area, including fibroblasts, in an upper channel with microvascular endothelial cells in a lower channel, e.g. showing a cut away view of multiple areas as part of one spiral channel.

An exemplary schematic of one embodiment of an open top chip as a 3D Alveolus Lung On-Chip is shown in FIG. 3.

FIG. 3 An exemplary schematic shows one embodiment of a 3D Alveolus Lung On-Chip demonstrating an air layer on top of an alveolar epithelium layer overlaying a stromal area, including fibroblasts, in an upper channel with microvascular endothelial cells in a lower channel, e.g. showing a cut away view of multiple areas as part of one spiral channel.

FIG. 4A-C An exemplary schematic shows one embodiment of a 3D Alveolus Lung On-Chip demonstrating locations of ports and input channels leading into the main growing chamber in relation to cell layers. FIG. 4A Overview of Epithelial surface (upper channel) showing exemplary primary adult human alveolar epithelial cells seeded on ECM made of Collagen IV, Fibronectin and Laminin. FIG. 4B Overview of Vascular compartment (lower channel) showing exemplary primary adult microvascular endothelial cells are seeded on ECM made of Collagen IV and Fibronectin. FIG. 4C An expanded side view of Tridimensional stroma showing exemplary primary adult human fibroblasts embedded within the stromal compartment.

A. Open Top Microfluidic Chips without Gels.

In one embodiment, open top organ-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips with Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel. In one embodiment, the open-top microfluidic device does contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic chips comprise lumens formed by viscous fingering described herein for closed top chips.

Lumen gel structures may be used in several types of embodiments for open top microfluidic chips, e.g. epithelial cells can be attached to outside of the gel, or within the gel. In some embodiments, LPDCs may be added within the gel, or below the gel. In some embodiments, stromal cells are added within the gel. In some embodiments, stromal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels.

EXAMPLES

The following examples illustrate some embodiments and Embodiments described herein. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1—Alveolus Lung On-Chip: Evaluation of Epithelial Cells in the Upper Compartment In one embodiment, an exemplary timeline was used for preparing, seeding, and evaluating an Alveolus Lung-On-Chip. FIG. 5 shows an exemplary schematic of one embodiment of an experimental timeline where Gel preparation is on Day-2; ECM is added to microchannels on Day-1; Cell seeding is on Day 0; Air-Liquid Interface is established by Day 5; Stretch of 4% begins on Day 9; Stretch of 10% begins on Day 12 which may continue up to Day 15. Cell seeding included fibroblast cells within a gel, alveolar epithelial cells overlaying the gel in the upper channel, and endothelial cells in the lower channel. Incorporation of more physiologically relevant ECM (Elastin).

In some embodiments, mechanical stretch was providing using vacuum applied to vacuum channels for moving the membrane within the chip simulating in vivo breathing movements. In some embodiments, read-outs, i.e. evaluation, includes but is not limited to: on-chip immunostaining, e.g. Type I and Type II pneumocytes; on-chip chemical staining, e.g. DAPI (4',6-Diamidino-2-Phenylindole, Dihydrochloride) for identifying nucleic acids, such as in cell nuclei; removal of tissue from the chip for microscopic evaluation after fixation, embedding, sectioning, and staining of tissues, e.g., H&E stain (i.e. Haemotoxylin and Eosin) comprising two dyes: haemotoxylin (blue/purple stain) for staining nuclei and eosin (pink stain) for staining acidophilic components in the tissue; mRNA expression in cells on-chip, including but not limited to RNAseq analysis, etc.

Thus, in one embodiment, an epithelial compartment on-chip was found to comprise Type I and Type II alveolar cells at 15 days post seeding. Further, epithelial cells on-chip formed an intact monolayer expressing cell-cell junction markers (E-cadherin, Connexin 43) and ion transporters (Na+ channels). A stromal compartment on-chip composed of fibroblasts embedded in 3D gel was discovered to remain stable over the entire course of the experiment, with the majority of fibroblasts staining positive for viable cell markers after 2 weeks in culture. H&E staining of tissues grown on-chip revealed preferential localization of fibroblasts beneath the epithelial layer. Moreover, microvascular lung endothelial cells on-chip formed a compact monolayer across the entire length of the vascular channel.

In fact, the inventors believe the ability to maintain primary human adult alveolar cells for 15 days, including up to 10 days under an ALI (i.e. air-liquid interface), in vitro, may be a novel finding. Furthermore, the co-cultivation of fibroblasts with alveolar epithelial cells promoted expression of epithelial markers such as Surfactant B and Aquaporin 5.

The following exemplary figures demonstrate these discoveries.

FIG. 6A-B shows an exemplary schematic and micrographs of one embodiment of an epithelial surface: comprising alveolar epithelial cells forming a compact monolayer at 15 days post seeding. FIG. 6A shows an exemplary schematic of an open top chip with an exemplary micrograph of stained cells within the central chamber. FIG. 6B shows an enlarged view of the exemplary micrograph showing stained (red) Type I-Like pneumocytes co-stained for Actin (green); Nuclei (blue).

FIG. 7 Shows an exemplary micrograph of an Epithelial layer growing on/within a gel layer in a Alveolus 3D gel system showing exemplary tissue architecture as a H&E stained alveolar cells. Thus, providing an epithelial surface in one embodiment of a 3D gel system on-chip further demonstrating the capability to support interaction of epithelial cells, endothelial cells, and fibroblast cells within a chip.

A mixed population of Type I and Type II pneumocytes are present on-chip 2 weeks post seeding. FIGS. 8A-B Show exemplary micrographs demonstrating the detection of Type I and Type II Pneumocytes. HTI-56—Type I (red); HTII-280—Type II (green) and DAPI stained—Nuclei (blue). FIG. 8A shows a co-stained area on-chip while the micrographs in FIG. 8B shows enlarged micrographs, using different filters, of the area outlined in white dotted line in FIG. 8A. Upper, micrograph showing both cell types in relation to nuclei; middle, micrograph showing Type I cells (red) in relation to nuclei; and lower, micrograph showing Type II cells (green) in relation to nuclei.

The presence of Type I-like and Type II pneumocytes were found using specific cellular markers. FIGS. 9A-B Show exemplary micrographs further demonstrating the presence of Type I-like and Type II pneumocytes on-chip using specific cellular markers, e.g. FIG. 9A pneumocyte Markers Mature Surfactant C Type II (green) and FIG. 9B Podoplanin Type I (red) in relation to nuclei (blue).

Alveolar epithelial cells display basolateral localization of E-Cadherin and Na/K-pump (Na+/K+ pump) at 15 days post seeding. FIGS. 10A-C Shows exemplary micrographs further demonstrating the presence of E-Cadherin and Na/K-pump proteins at 15 days post seeding. FIG. 10A An exemplary micrograph showing triple stained cells on-chip: Na+/K+-pump (red); E-Cadherin (green); Nuclei (blue). FIG. 10B An exemplary micrograph showing Na+/K+-pump (red). FIG. 10C An exemplary micrograph showing E-Cadherin (green).

Epithelial cells express ENaC (scnn1) 15 days post seeding. FIG. 11 Shows exemplary micrographs further demonstrating the presence of Epithelial Na+ channels (ENaC). E-Cadherin (green); EnaC (pink); and Nuclei (blue). Right micrograph is an enlargement of the area outlined in white dashes in the left micrograph. Connexin 43 is expressed on-chip 15 days post seeding.

FIGS. 12A-B Show exemplary micrographs demonstrating the presence of Connexin 43—Gap Junction. Connexin 43 (grey); Nuclei (blue). FIG. 12A shows co-stained cells. FIG. 12A-B Shows Connexin 43 (grey) staining where yellow arrows point to individual cells.

Example 2—Alveolus Lung On-Chip: Evaluation of Stromal Cells in the Stromal Compartment Human primary lung fibroblasts have been incorporated within the 3D stromal compartment of the chip, see highlighted area on-chip shown in FIG. 4C. Incorporation of Lung Fibroblasts On-Chip rhodamine phalloidin (PHDR1) Alexa Fluor® 488 Phalloidin binds to F-actin proteins.

FIGS. 13A-B Show exemplary micrographs demonstrating the presence of lung fibroblasts. FIG. 13A lung fibroblasts stained for Phalloidin (pink) and Nuclei (blue). FIG. 13B Phalloidin (pink) and Type I-Like cells (green). White Bar=100 um.

FIGS. 14A-C Show exemplary micrographs demonstrating assessment of Fibroblast Viability growing on-chip. FIG. 14A Maximum intensity projection of Z-Stack. FIG. 14B Live/Dead. FIG. 14C Phase Contrast (left) Phase Contrast Merge with Live/Dead. Live/dead staining shows high percentage of cell surviving on chip on day 15 post-seeding. Dead fibroblasts: rounded morphology and red nuclei. Live fibroblasts: typical elongated morphology and green cytoplasm.

FIGS. 15A-B Show exemplary micrographs demonstrating Distribution and Morphology of Alveolar Fibroblasts On-Chip. Fibroblasts are mostly localized underneath the epithelial surface, FIG. 15A, and display typical stellate shape, FIG. 15B.

Confocal Imaging at the Epithelial-Stromal Interface. FIGS. 16A-B Shows exemplary micrographs demonstrating Fibroblasts protrude towards the alveolar epithelium. FIG. 16A Type I (red) Type II (green) Fibroblasts (red) Nuclei (blue). FIG. 16B 3D animation.

Studies of the contribution of fibroblasts to epithelial cell maturation: Fibroblast-Epithelial Cell Interaction. FIG. 20 Shows exemplary graph comparing gene expression of epithelial cells with and without fibroblast cells seeded into the stromal compartment. Gene expression at 15 days in culture.

Example 3—Alveolus Lung On-Chip: Evaluation of the Lower Vascular Compartment

FIG. 17 Shows exemplary micrographs demonstrating microvascular endothelial cells expressing typical endothelial cells markers and covering the entire surface of vascular channel at 2 post seeding. Left to right: PECAM-1; VE-Cadherin; and VWF.

Example 4—Alveolus Lung On-Chip: Effect of Mechanical Force on the Alveolus Lung On-Chip In one embodiment of an alveolus Lung On-Chip, cells growing on-chip are exposed to both flow and stretching, as nonlimiting embodiments for growing under conditions of a mechanoactive environment. After growing under these conditions, i.e. alveolar cells grown for 15 days in mechanoactive environment (under constant flow and stretching) in Open-Top-Chips are positively stained with specific Type I and Type II antibodies (i.e. HTI/HTII). The stability of stromal compartment did not appear to be affected by stretch (as assessed at 15 days of stretch).

Mechanical strain promotes expression of Type II cell marker (HTII-Type II marker HT-II 280). FIGS. 18A-E Show exemplary micrographs demonstrating effect of mechanical strain on epithelial cells while FIG. 18E shows a graph comparing the expression of these markers on cells, with and without strain. FIGS. 18A/B Without strain. FIG. 18C/D with 10% Strain. Stained Type I cells are shown in red. Stained Type II cells are shown in green. FIG. 18E shows that strain increases expression of the HTII cell marker. Fluorescence Intensity per field view (a.u.) HTI vs. HTII.

Breathing motion (i.e. membrane under strain resulting in the movement of the cell layers) increases the number of Type II cells in the epithelia layer bringing the percentages closer to physiologically relevant proportions of Type II/Type I pneumocytes in vivo (40% vs. 60%, respectively).

FIG. 19A-B Shows exemplary graphs showing an exemplary effect of breathing motion on increasing expression of the Type II marker HT-II 280 vs. Type I markers.

FIG. 19A No strain resulting in 27% vs. 73%, respectively; and FIG. 19B Membrane under strain resulting in 44% vs. 56%, respectively.

Example 5—Alveolus Lung On-Chip: Effect of ECM Composition on Epithelial Cells

1. ECM: Effects on Gene Expression.

Gene expression data confirms that a combination of Collagen (ColI) IV, Fibronectin (FN) and Laminin (L) on-chip supports expression of both Type I (Aquaporin 5) and Type II pneumocytes (Surfactant B) better than any other combination tested, see FIGS. 21A-D and 22A-B.

TABLE 1

Genetic Markers for Epithelial (Pneumocyte) Cell Types.

| Gene | Marker for |
|---|---|
| Pdpn | Type 1 |
| HOPX | Type 1 |
| Aquaporin 5 | Type 1 |
| Pro-surfactant B | Type II |
| ABCA3 | Type II |
| Tgf-p | Epithelial to mesenchymal transition (EMT) |

FIGS. 21A-D Shows exemplary effects of different ECM Composition on Epithelial Cells. FIGS. 21A-C shows HTI-56 (Type I-Like cells) (red) and HTII-280 (Type II cells) (green) exposed to FIG. 21A ColI I; FIG. 21B ColI IV; FIG. 21C ColI IV-FN-L. FIG. 21D shows a graphical comparison markers demonstrating segregation of Type I-Like and Type II cell markers.

FIGS. 22A-B Show an exemplary gene expression of markers for FIG. 22A Type II Epithelial Cells and FIG. 22B Type I Epithelial Cells.

Example 6—ECM: Effect of Elastin on Stromal Compartment

As shown herein, a combination of Collagen IV, Fibronectin and Laminin promoted the expression and clear segregation of both Type I/Type II cell markers, see FIG. 21A-D.

Furthermore, a physiologically relevant concentration of elastin within the stromal compartment (20% Elastin-70% Bovine-collagen) was tested for its effects on cells growing on-chip. In fact, 70% (416 Chips tested) of the elastin-enriched gels were stable for 15 days on-chip. ALI was maintained for 10 days without compromising gel stability. Thus, cells growing on Collagen or Elastin-rich gel show comparable levels of viability. However, Elastin-rich gels appeared to promote more even (regular) cell morphology, see, FIGS. 23B-C.

FIGS. 23A-C FIG. 23A Shows an exemplary schematic timeline for use with a paraformaldehyde (PFA) fixed cell based readout. FIG. 23B Exemplary cell staining after growing on a ColI I Gel. FIG. 23C Exemplary cell staining after growing on a CoiI I+Elastin (30%) Gel. Live cells (green), dead cells (debris) (red), nuclei (blue).

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method comprising:
    (a) providing a first microfluidic device comprising
        i) a first fluidic channel in fluidic communication with a second microfluidic channel, with a semi-permeable membrane disposed between said first and second microfluidic channels,
        ii) first cells comprising at least one parenchymal cell type, said first cells are positioned in said first microfluidic channel or said second microfluidic channel, and
        iii) second cells comprising at least one stromal cell type, said second cells are positioned in said first microfluidic channel or said second microfluidic channel, wherein said stromal cell type is a lamina propria-derived cell; and
    (b) perfusing said first microfluidic device with fluid.

2. The method of claim 1, wherein said parenchymal cell type is selected from the group consisting of epithelial cells of the lung, epithelial cells of the skin and epithelial cells of the urogenital tract.

3. The method of claim 2, wherein said epithelial cells of the lung are selected from the group consisting of alveolar epithelial cells and airway epithelial cells.

4. The method of claim 1, wherein at least one of said first cells and second cells comprise cells derived from a tumor.

5. The method of claim 1, wherein at least one of said first cells and second cells comprise cells derived from a region in or around a tumor.

6. The method of claim 1, wherein at least one of said first cells and second cells comprise cells from a region of inflammation.

7. The method of claim 1, wherein at least a portion of said second cells are disposed in contact with said semi-permeable membrane.

8. The method of claim 1, wherein the device further comprises a gel.

9. The method of claim 8, wherein at least a portion of said second cells are disposed within said gel.

10. The method of claim 1, wherein said device further comprises a removable top.

11. The method of claim 10, wherein said method further comprises c) removing said removable top.

12. The method of claim 1, wherein said device further comprises an open region in contact with at least one of said first fluidic channel, said semi-permeable membrane, said first cells, or said second cells.

13. The method of claim 1, further comprising c) contacting said first cells, said second cells or both with a first agent.

14. The method of claim 13, further comprising d) detecting at least one response to said first agent.

15. The method of claim 14, wherein the said at least one response comprises modulation of the inflammation reaction.

16. The method of claim 14, wherein the said at least one response comprises modulation of cytokine profile.

17. The method of claim 14, wherein the said at least one response comprises modulation of gene expression.

18. The method of claim 14, wherein the said at least one response comprises modulation of cell or tissue morphology.

19. The method of claim 13, wherein said first agent causes an inflammatory reaction.

20. The method of claim 19, wherein the method further comprises d) contacting said first cells, said second cells or both with a second agent.

21. The method of claim 20, wherein the method further comprises e) detecting inhibition of said inflammatory reaction by said second agent.

22. The method of claim 21, wherein the method further comprises f) comparing the degree of inhibition by said second agent with said second cells of a first patient with the degree of inhibition by said second agent with second cells of a second patient.

23. The method of claim 21, wherein the method further comprises f) comparing the degree of inhibition by said second agent with said second cells of a first organ with the degree of inhibition by said second agent with second cells of a second organ.

24. The method of claim 21, wherein the method further comprises f) comparing the degree of inhibition by said second agent with said second cells of a first region of an organ with the degree of inhibition by said second agent with second cells of a second region of an organ.

25. The method of claim 1, wherein said lamina propria-derived cell is viable after culture for 2 weeks in said micro fluidic device.

26. The method of claim 1, wherein said parenchymal cell type expresses a higher level of parenchymal cell marker in the presence of said lamina propria-derived cell than in the absence of said of said lamina propria-derived cell.

* * * * *